United States Patent
Jones et al.

(10) Patent No.: US 7,418,961 B2
(45) Date of Patent: Sep. 2, 2008

(54) DISPENSING APPARATUS

(75) Inventors: Matthew Meredith Jones, Warwickshire (GB); Christopher John Jones, Warwickshire (GB); Robert Frederick Veasey, Warwickshire (GB)

(73) Assignee: Bespak plc, Norfolk (GB)

( * ) Notice: Subject to any disclaimer, the term of this patent is extended or adjusted under 35 U.S.C. 154(b) by 132 days.

(21) Appl. No.: 10/545,026

(22) PCT Filed: Feb. 10, 2004

(86) PCT No.: PCT/GB2004/000545

§ 371 (c)(1),
(2), (4) Date: Jul. 24, 2006

(87) PCT Pub. No.: WO2004/071562

PCT Pub. Date: Aug. 26, 2004

(65) Prior Publication Data
US 2006/0283444 A1    Dec. 21, 2006

(30) Foreign Application Priority Data
Feb. 11, 2003 (GB) .................................. 0303092.1

(51) Int. Cl.
*A61M 11/00* (2006.01)
(52) U.S. Cl. ..................... 128/200.14; 128/200.23; 222/649
(58) Field of Classification Search .......... 128/200.23, 128/200.14; 222/649, 639, 645–648
See application file for complete search history.

(56) References Cited

U.S. PATENT DOCUMENTS

| | | | |
|---|---|---|---|
| 4,674,651 A | 6/1987 | Scidmore et al. | |
| 5,027,808 A | 7/1991 | Rich et al. | |
| 5,060,643 A | 10/1991 | Rich et al. | |
| 5,284,133 A * | 2/1994 | Burns et al. | 128/200.23 |
| 5,408,994 A | 4/1995 | Wass et al. | |
| 5,487,378 A | 1/1996 | Robertson et al. | |
| 5,823,178 A * | 10/1998 | Lloyd et al. | 128/200.14 |
| 5,840,279 A | 11/1998 | Narodylo et al. | |
| 6,460,537 B1 | 10/2002 | Bryant et al. | |
| 6,990,975 B1 * | 1/2006 | Jones et al. | 128/200.23 |
| 7,036,505 B2 * | 5/2006 | Bacon et al. | 128/203.13 |
| 2002/0189612 A1 | 12/2002 | Rand | |

FOREIGN PATENT DOCUMENTS

| | | |
|---|---|---|
| GB | 2 381 460 | 5/2003 |
| WO | 93/24167 | 12/1993 |
| WO | WO93/24167 | 12/1993 |
| WO | 94/16759 | 8/1994 |

(Continued)

*Primary Examiner*—Steven O. Douglas
(74) *Attorney, Agent, or Firm*—Smith, Gambrell & Russell LLP

(57) ABSTRACT

Dispensing apparatus comprising a housing for receiving in use a dispensing container (100) containing a product, the housing comprising an outlet through which said product, in use, is dispensed, wherein the dispensing apparatus further comprises a trigger mechanism (7) for controlling actuation of a dispensing container (100) received in the housing, the trigger mechanism (7) comprising a pivotable member (74) rotatable from a first position to a second position, wherein the dispensing apparatus further comprises lock-out means movable from a locked position, in which rotation of the pivotable member from its first position to its second position is prevented, to an unlocked position, in which the pivotable member (74) is free to rotate.

19 Claims, 29 Drawing Sheets

FOREIGN PATENT DOCUMENTS

| | | |
|---|---|---|
| WO | WO94/16759 | 8/1994 |
| WO | 99/49916 | 10/1999 |
| WO | WO99/49916 | 10/1999 |
| WO | 01/70316 | 9/2001 |
| WO | 02/26300 | 4/2002 |

* cited by examiner

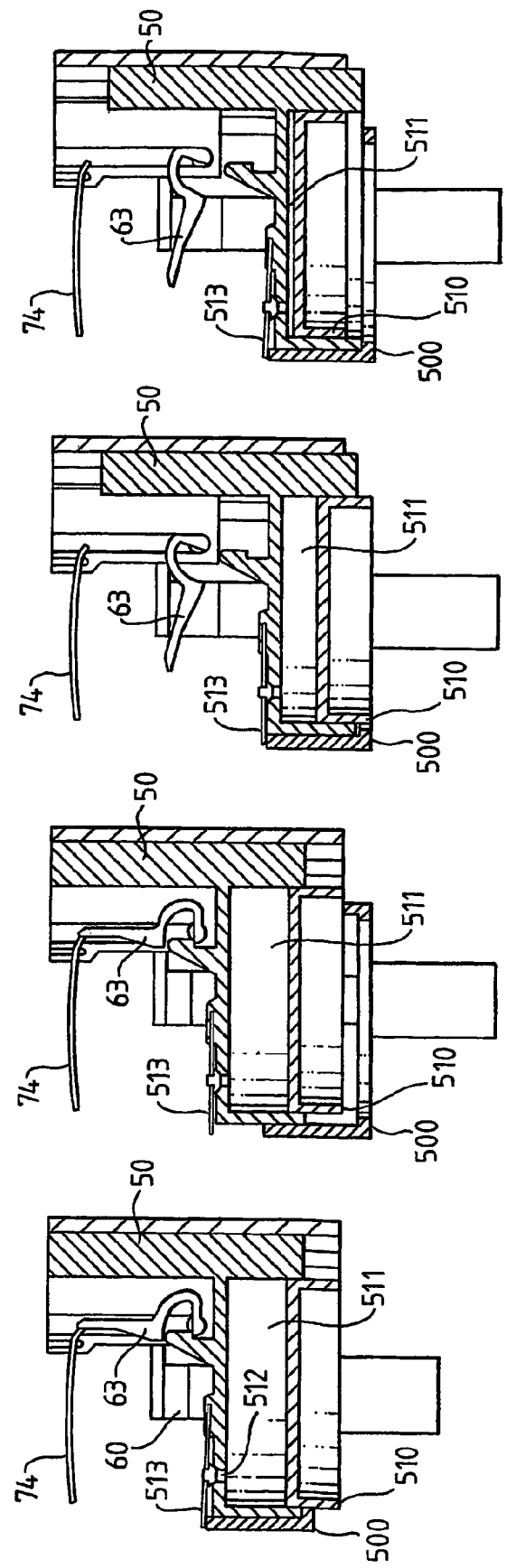

DISPENSING APPARATUS

The present invention relates to a dispensing apparatus, in particular but not exclusively, a dispensing apparatus for dispensing medicaments.

Dispensing apparatus are known for use in dispensing medicaments. The medicaments dispensed may be any of a wide range of known substances. Many such medicaments may be harmful if taken in too large a quantity or by the wrong person. Consequently, many medicaments are only available via prescription from an authorised medical practitioner. Prescribed medicaments of this type are prescribed to specific individuals and at certain dosage levels. Some medicaments, especially those used for pain relief, may be extremely harmful if taken in too large a quantity. However, it is also often the case that a patient may wish some flexibility in the timing of the doses that can be administered in order to maximize the beneficial effect of the medicament.

According to the present invention there is provided a dispensing apparatus comprising a housing for receiving in use a dispensing container containing a product, the housing comprising an outlet through which said product, in use, is dispensed, wherein the dispensing apparatus further comprises a trigger mechanism for controlling actuation of a dispensing container received in the housing, the trigger mechanism comprising a pivotable member rotatable from a first position to a second position, wherein the dispensing apparatus further comprises lock-out means movable from a locked position, in which rotation of the pivotable member from its first position to its second position is prevented, to an unlocked position, in which the pivotable member is free to rotate.

Preferably the lock-out means comprises a lock-out member movable into and out of engagement with the pivotable member.

Preferably, the lock-out member comprises an elongate stem movable axially within the housing and a transverse arm extending laterally from the elongate stem, wherein a distal end of the transverse arm is engagable with the pivotable member.

In one embodiment, the pivotable member is a vane. Preferably, the apparatus further comprises at least one air inlet for entry of air into an interior of the housing, wherein the vane is rotatable when suction is applied to the at least one air inlet to establish an air flow through the interior of the apparatus.

Preferably, the lock-out member is movable by means of a motor.

Preferably, the lock-out member comprises a threaded portion which engages a threaded rotatable member of the motor.

The dispensing apparatus may further comprise control means for controlling operation of the motor. Preferably, the control means comprises a control processor mounted within the housing. Preferably, the control means further comprises one or more switches operable by the lock-out member to send signals to the control processor regarding the position of the lock-out member. The lock-out member may comprise one or more cam surfaces for engaging and switching the one or more switches of the control means on movement of the lock-out member.

Advantageously, the lock-out member further comprises means for locking a first part and a second part of the housing together. Preferably, the lock-out member is mounted to one of the first or second parts of the housing and the means for locking the first and second parts together comprises a distal end of the lock-out member which is engagable in a recess in the other of the first or second parts.

The dispensing device may further comprise a dispensing container. The dispensing container may be a metered dose inhaler. The dispensing container may contain a medicament for oral or nasal administration. Preferably, the dispensing container includes a hydrofluoroalkane propellant.

The present invention also provides a method of controlling operation of a dispensing apparatus of the type comprising a housing for receiving in use a dispensing container containing a product, and a trigger mechanism comprising a pivotable member rotatable from a first position to a second position, the method comprising the steps of:

moving a lock-out means from a locked position, in which rotation of the pivotable member from its first position to its second position is prevented, to an unlocked position, in which the pivotable member is free to rotate;

applying suction to an outlet of the dispensing apparatus to establish a flow of air from the at least one air inlet to the outlet to move the pivotable member from its first position to its second position to trigger the trigger mechanism to dispense a product from said dispensing container;

moving the lock-out means from the unlocked position back to the locked position to prevent further rotation of the pivotable member after resetting the dispensing apparatus.

The present invention further provides a method of controlling the timing of actuation of a dispensing apparatus of the type comprising a housing for receiving in use a dispensing container, comprising the steps of:

providing a timing mechanism;
starting the timing mechanism on a first actuation of the dispensing apparatus to commence timing of a first actuation 'window' of predetermined length;
optionally actuating the dispensing apparatus one or more times during the actuation 'window', wherein on each actuation of the dispensing container the timing of a further actuation 'window' is commenced;
wherein if a total number of actuations during any actuation 'window' reaches a predetermined number further actuation of the dispensing apparatus is prevented until the end of said actuation 'window'.

Optionally, successive actuations of the dispensing apparatus are prevented within a fixed time period of each other.

Embodiments of the present invention will now be described, by way of example only, with reference to the following drawings in which:

FIGS. 37 to 40 are cross-sectional views through a portion of a device according to the present invention showing an alternative mechanism for removing valve load from a pressurised dispensing, container;

Figure 1:
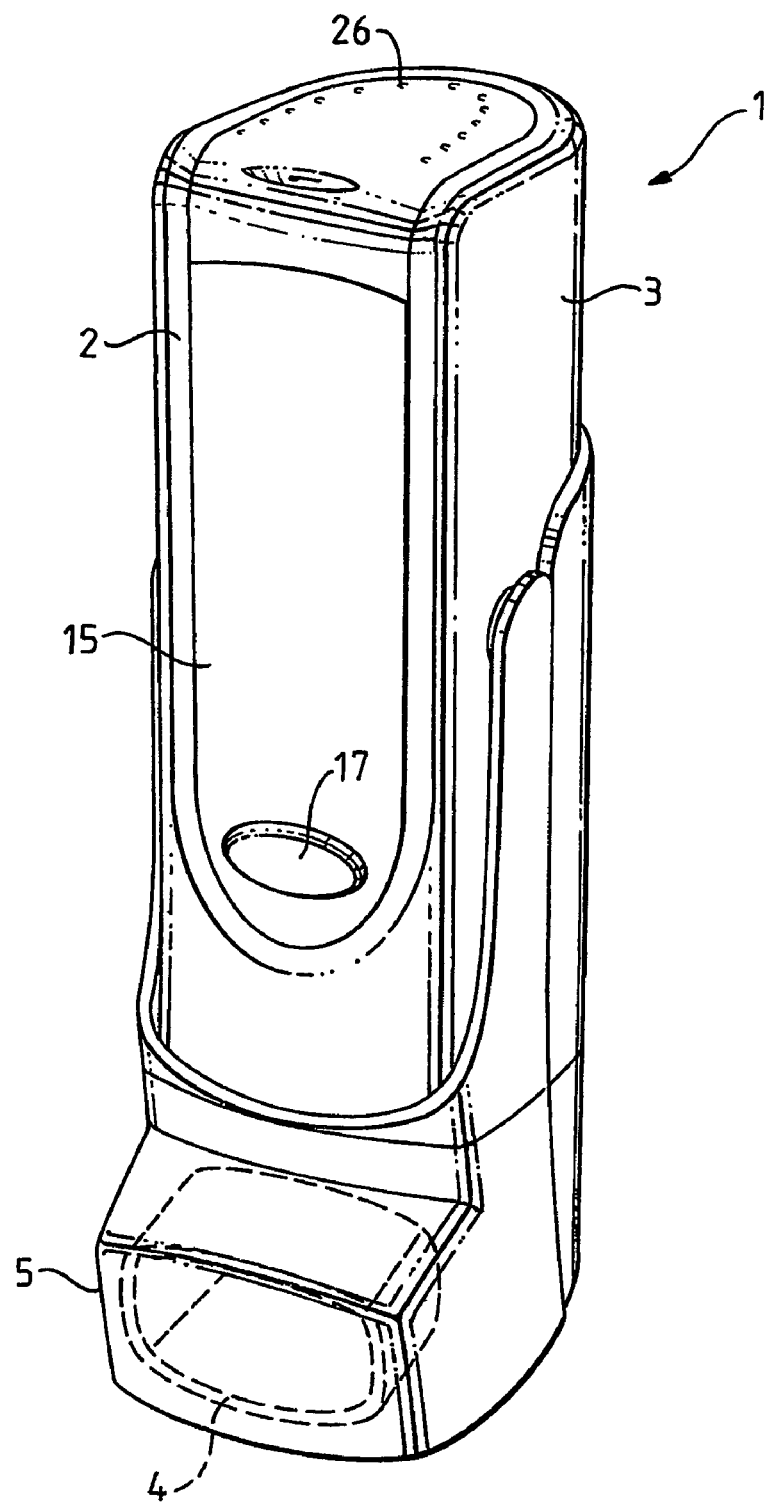
FIG. 1 is a perspective view of a first embodiment of dispensing device according to the present invention.

The first embodiment of the dispensing device of the present invention is shown in FIGS. 1 to 17. This embodiment is particularly suitable for a reusable device. As shown in FIG. 1, the dispensing device generally comprises an actuator 1 in which is received a pressurised dispensing container containing a medicament or other substance which is to be dispensed. The actuator 1 comprises a housing formed from a front case 2 and a rear case 3, a mouthpiece 4 and a dust cap 5.

Figure 2:
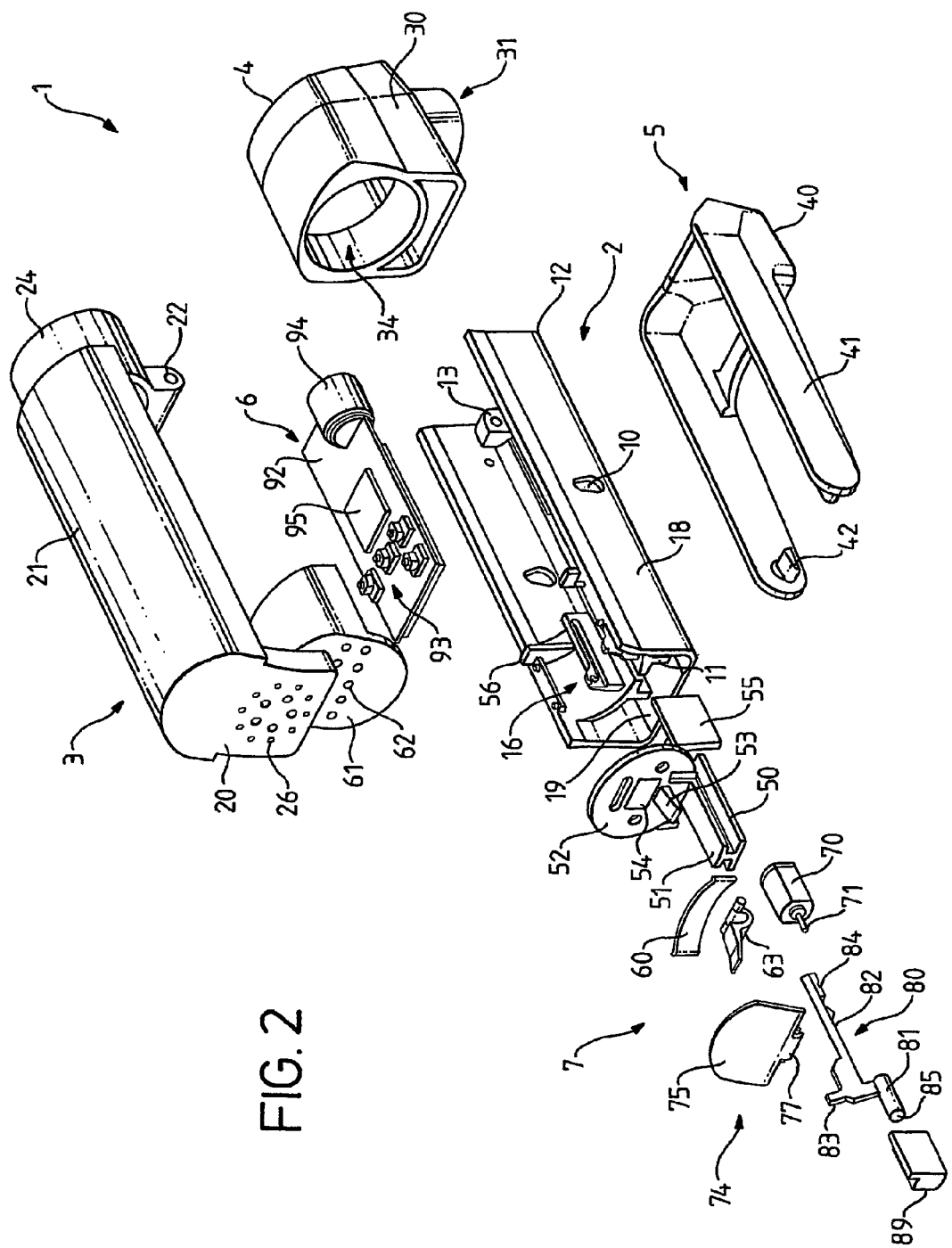
FIG. 2 is an exploded perspective view of the device of FIG. 1.
Figure 13:
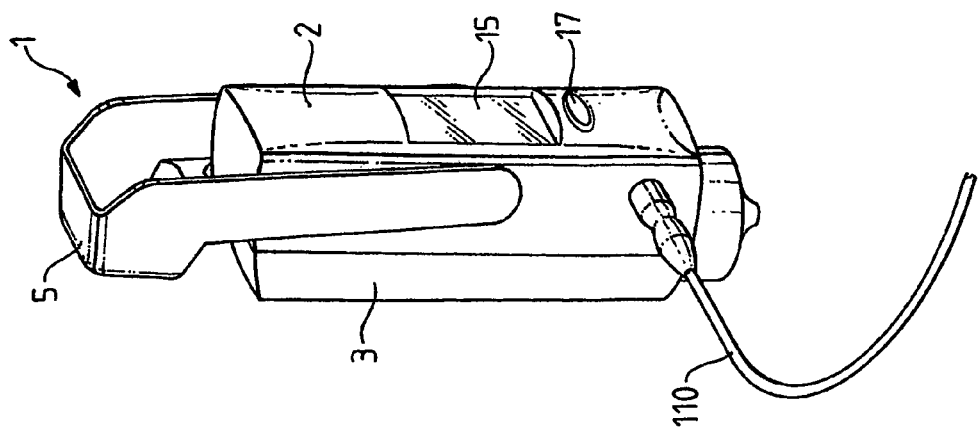
FIGS. 11 to 15 are perspective views of the device illustrating the replacement of a pressurised dispensing container within the device.

As shown in FIG. 2, the front case 2 comprises a body portion 12 having the general form of an open channel having two side walls 18 extending from a rear wall 19. An interior of the front case 2 is provided with a chassis 16 formed integrally with the front case 2 and to which other components of the actuator 1 are fixed during assembly. A portion of the chassis 16 forms a canister seat guide rail 11, the use of which will be discussed below. At one end of the front case 2 there is provided a first portion 13 of a hinge. Two apertures 10 are formed in the side walls 18 approximately midway along the length of the front case 2. The front case comprises an aperture for receiving an LCD screen 15 as shown in FIG. 1. A data port 14 may also be provided in the front case 2 as shown in FIG. 13, the use of which will be discussed below.

Figure 7:
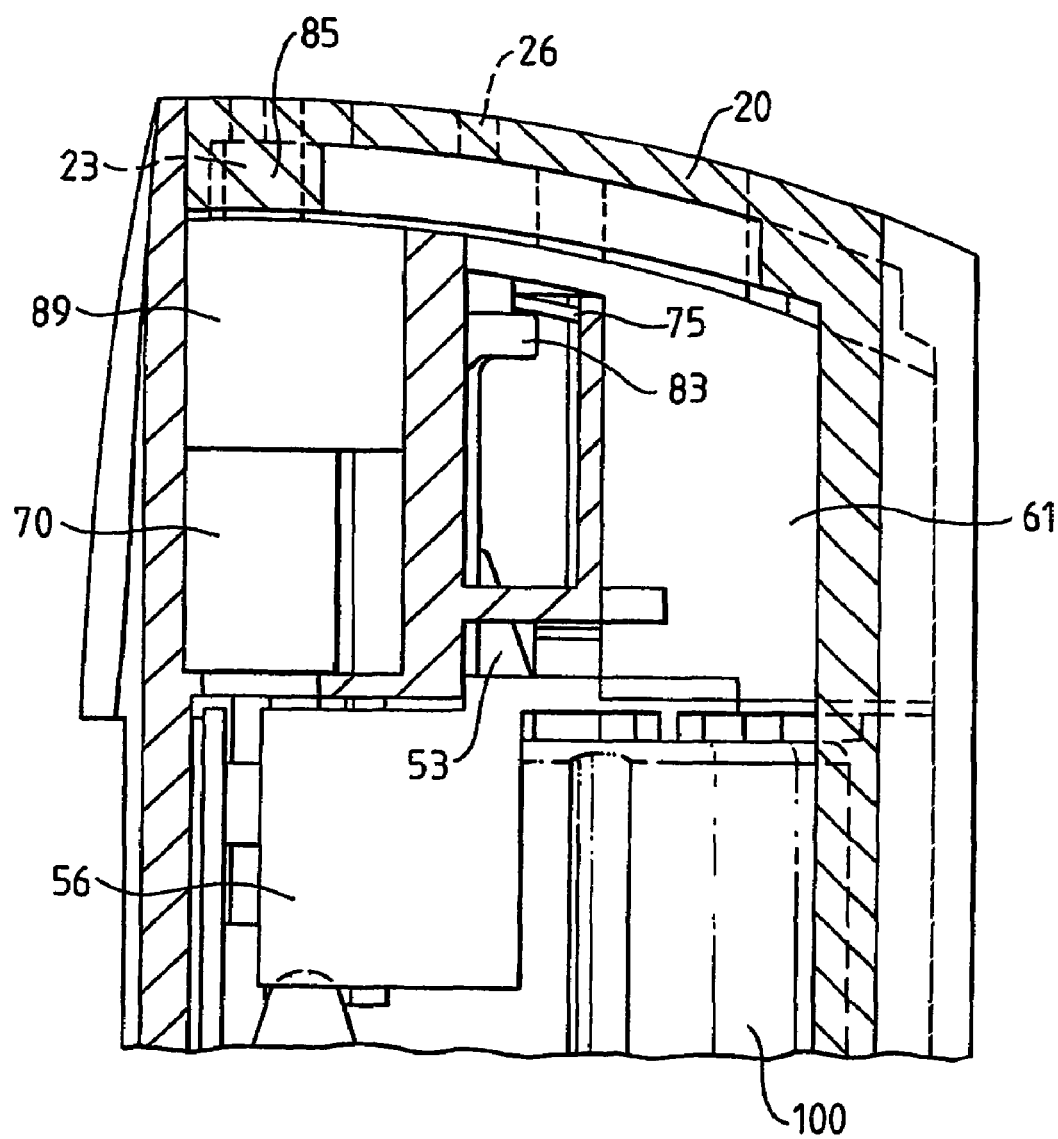
FIGS. 7 to 10 are cross-sectional views of a portion of the device of FIG. 1 showing the device in locked, armed, unlocked and opened states.
Figure 10:
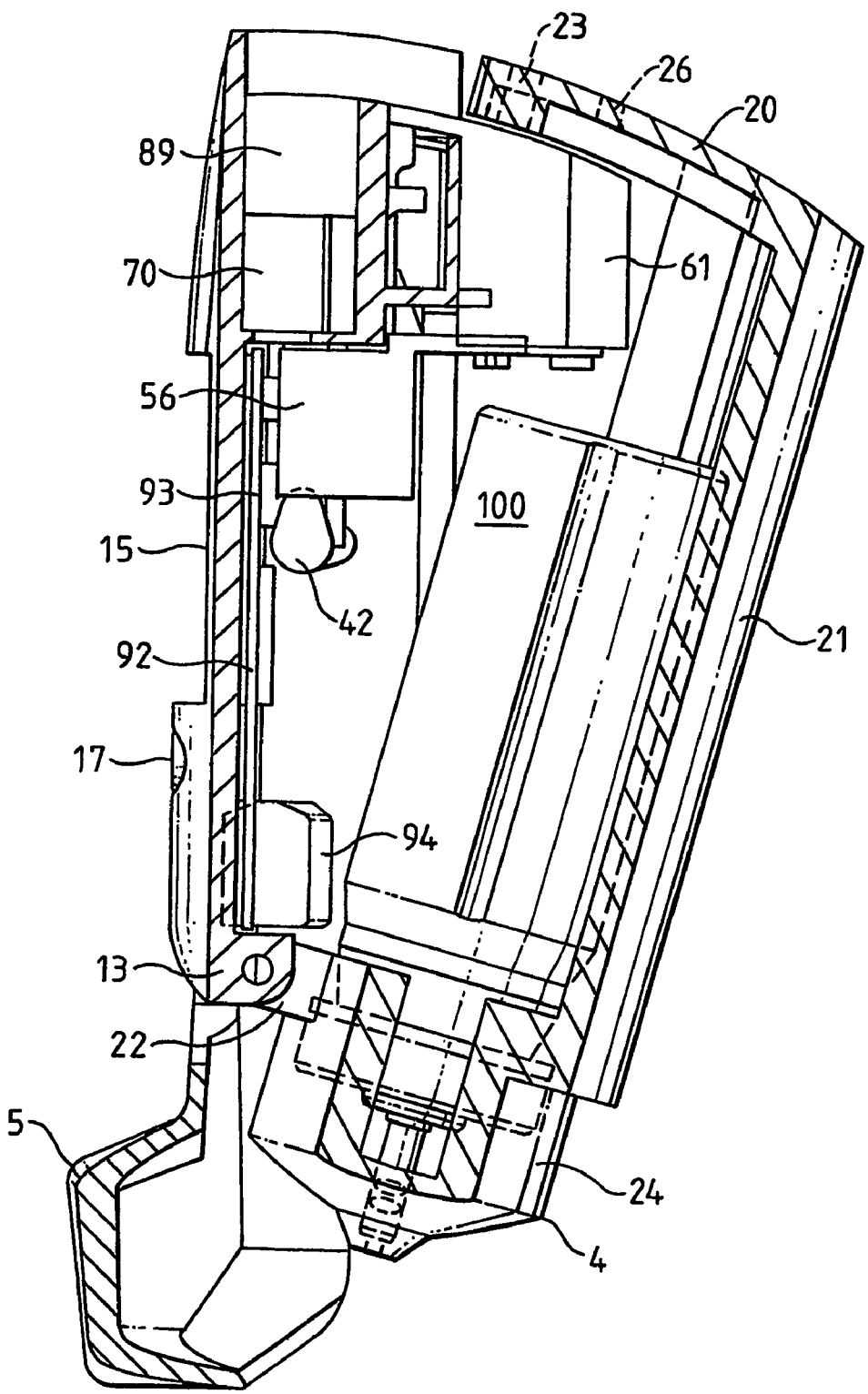

The rear case 20 comprises a body portion 21 having at one end a top portion 20 and at the other end a stem portion 24 terminating in a conical portion 25 shown in FIG. 10. On or near the stem portion 24 there is provided a second portion 22 of a hinge. During assembly the first portion 13 of the hinge and the second portion 22 of the hinge cooperate with one another to pivotally join the front case 2 and the rear case 3 together. Preferably the first portion 13 and the second portion 22 of the hinge are permanently pivoted together by means of a through bolt or similar. The top portion 20 of the rear case 3 is provided with a plurality of air inlet holes 26. An internal face of the top portion 20 is also provided with a locking recess 23 as best shown in FIG. 7.

Figure 12:
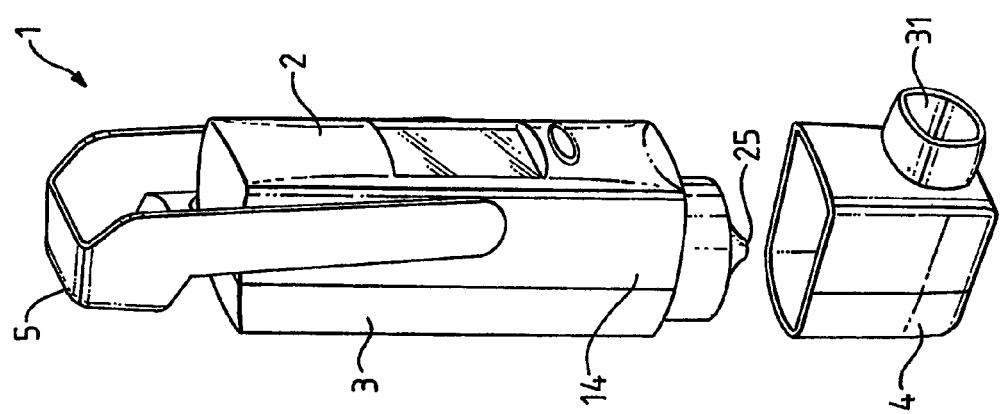
Figure 11:
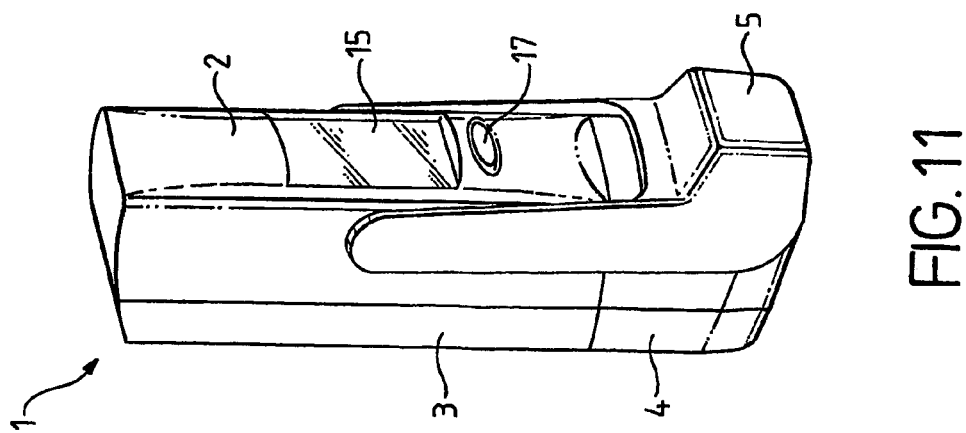

The mouthpiece 4 is detachable from the front case 2 and rear case 3. Advantageously the front case 2 and rear case 3 are shaped such that even with the mouthpiece 4 detached from the housing the interior of the housing containing the dispensing container 100 and trigger mechanism is not accessible as shown in FIGS. 10, 12 and 13. This prevents removal of the pressurised dispensing container 100 and also the insertion of foreign members into the interior of the housing and thus prevents tampering with the container. The mouthpiece 4 comprises a body 30 defining a mouthpiece outlet 31 directed generally laterally and a socket 34 which may be connected during assembly with the stem portion 24 of the rear case 3. The connection may be by means of a push fitting, a bayonet fitting, a screw threaded fitting or similar. An interior of the mouthpiece 4 is provided with a valve stem receiving block which receives in use a valve stem of a pressurised dispensing container received in the actuator 1. The valve stem block comprises an orifice for directing medicament dispensed from the pressurised dispensing container towards the outlet 31 of the mouthpiece 4 in a conventional manner.

The dust cap 5 comprises a mouthpiece cover 40 which is shaped to be received over and to cover the outlet 31 of the mouthpiece 4 and also preferably those areas of the mouthpiece 4 contacted in use by a user's mouth. The dust cap 5 further comprises two elongate arms 41 which extend from the mouthpiece cover 40 and are provided at the distal end with two inwardly directed bosses 42. The bosses 42 have a non-circular shape forming a cam surface. Alternatively, each boss 42 may be provided with an eccentrically positioned peg as described below with reference to the second embodiment. The dust cap 5 is assembled with the front case 2 by means of insertion of the bosses 42 through the apertures 10.

The actuator 1 is provided with a PCB (Printed Circuit Board) 6 which is connected to the chassis 16 of the front case 2. The PCB 6 is provided with a number of switches 93, a battery 94, a control processor 95 and the LCD 15.

The actuator 1 is further provided with a trigger mechanism 7 which is housed in an end of the actuator 1 remote from the mouthpiece 4. The trigger mechanism 7 comprises a canister seat 50, leaf spring 60, lock out motor 70, vane 74, shoot bolt 80 and shoot bolt slide 89.

The canister seat 50 comprises a transverse platform 52 of generally circular shape and an elongate beam 51 which extends upwardly from the transverse platform 52. The transverse platform 52 is provided with an upstanding hook 53 and a dished portion forming a spring seat 54. The canister seat 50 further comprises two flanges forming side guide walls 56. The canister seat 50 is assembled as a sliding fit in the front case 2 of the actuator with the elongate beam 51 forming a sliding fit with the canister seat guide rail 11. The side guide walls 55 and the guide rail 11 of the canister seat 50 ensure that the canister seat 50 is only able to move axially within the front case 2. The leaf spring 60 is held in position between the spring seat 54 of the canister seat 50 and two abutment surfaces 56 provided on the chassis 16 of the front case 2. The leaf spring 60 acts to bias the canister seat 50 towards the end of the front case 2 nearest the mouthpiece 4.

The slip hook 63 comprises an elongate arm 65 which extends from a pivot point 64. The elongate arm 65 includes an arcuate portion 66 near the pivot 64. The slip hook 63 also comprises a detent in the form of a catch surface 67 formed on an opposite side of the pivot point 64 from the elongate arm 65 as most clearly shown in FIG. 3. The distance from a distal end 69 of the elongate arm 65 to the pivot point 64 measured along the perpendicular to the line of action of the distal end 69 of the elongate arm 65 about the pivot point 64 is many multiples of the distance from the catch surface 67 to the pivot point 64 measured along the perpendicular to the line of action of the catch surface 67 about the pivot point 64.

Figure 3:
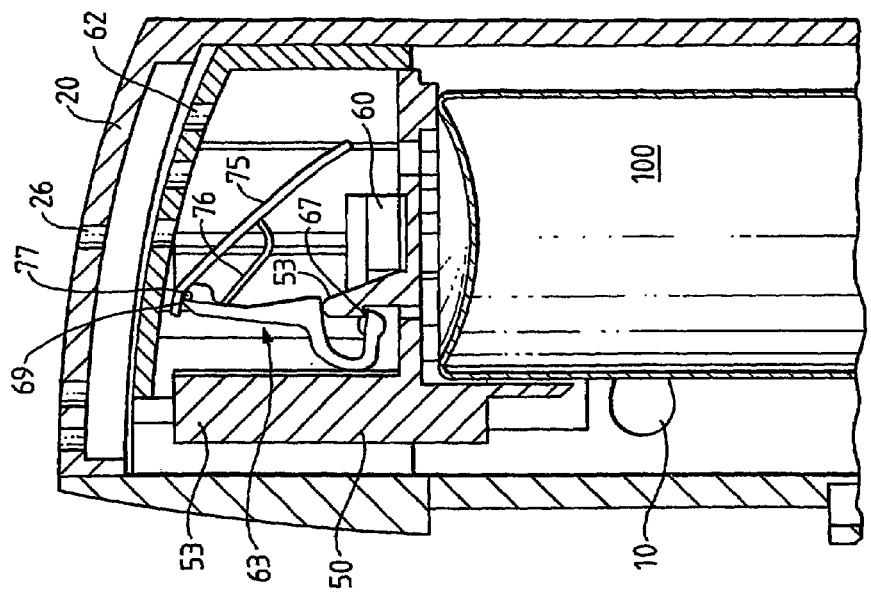
FIGS. 3 to 6 are cross-sectional views of a portion of the device of FIG. 1 showing the device during a typical dispensing and re-setting cycle.
Figure 4:
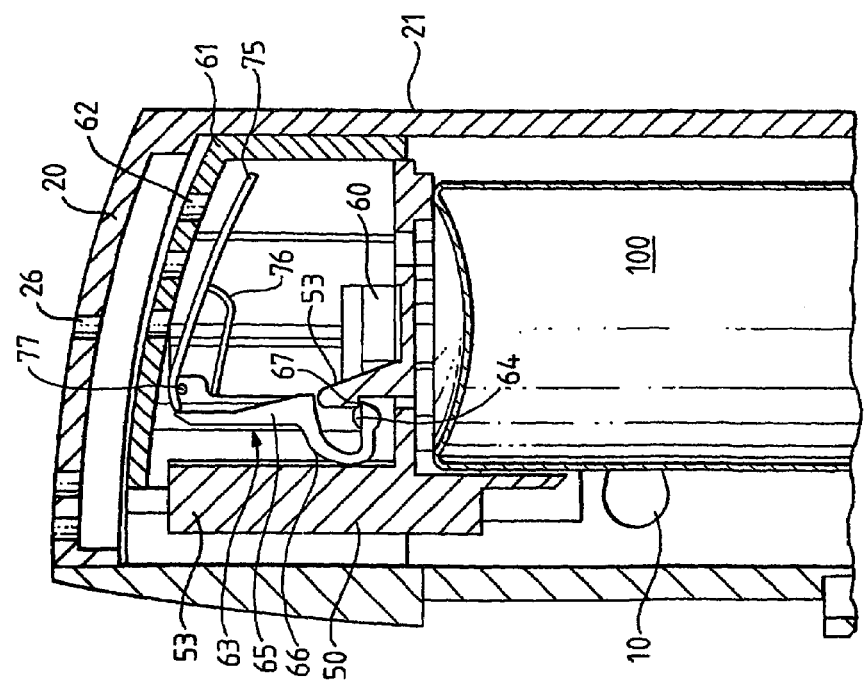

The slip hook 63 is freely rotatable in the clockwise and anti-clockwise directions as viewed in FIG. 3.

The lock-out motor. 70 comprises a rotatable lead screw 21 of conventional design.

The vane 74 comprises a body portion 75 of solid construction which pivots about a pivot point 77 connected to the front case chassis 16. An undersurface of the vane 74 is provided with a flexible plastic spring 76, the use of which will be described below.

The shoot bolt 80 comprises a stem 81 having an internally threaded bore (not shown) and an elongate member 82 extending from the stem 81 and comprising at its distal end a plurality of switch cams 84. The transverse arm 83 also extends laterally from the stem 81 towards vane 74.

The shoot bolt slide 89 is fixedly retained to the chassis 16 of the front case 2 and receives during assembly the shoot bolt stem 81 as a sliding fit.

A trigger cap 61 is provided attached to the front case 2. The trigger cap 61 comprises a plurality of air inlets 62. The trigger cap 61 covers the trigger mechanism 7 even when the front and rear cases 2, 3 are separated. It will be also noted, and as shown in FIG. 3, that the air inlets 62 of the trigger cap 61 are displaced relative to the air inlets 26 of the rear case 3 so as to prevent a foreign body being poked into the interior of the actuator 1 through the air inlets in order to tamper with the trigger mechanism 7.

FIG. 3 illustrates the trigger mechanism 7 and an upper end of the actuator 1 in the assembled condition with the trigger mechanism 7 ready for a dose to be dispensed from a pressurised dispenser container 100 received within the interior of the actuator 1. The pressurised dispensing container 100 is typically of the type having a metering valve with an internal spring bias. In the position shown in FIG. 3 the leaf spring 60 is compressed between the spring seat 54 and the abutment surfaces 56 and therefore acts to bias the canister seat 50 downwards towards the mouthpiece 4. Movement of the canister seat 50 is prevented by engagement of the hook 53 with the catch surface 67 of the slip hook 63. The body 75 of the vane 74 lies in close proximity to the air inlets 62 of the trigger cap 61. The flexible plastic spring 76 of the vane 74 is engaged against the chassis 16 of the front case 2 and biases the vane 74 with a light force upwardly into proximity with the air inlets 62.

Figure 5:
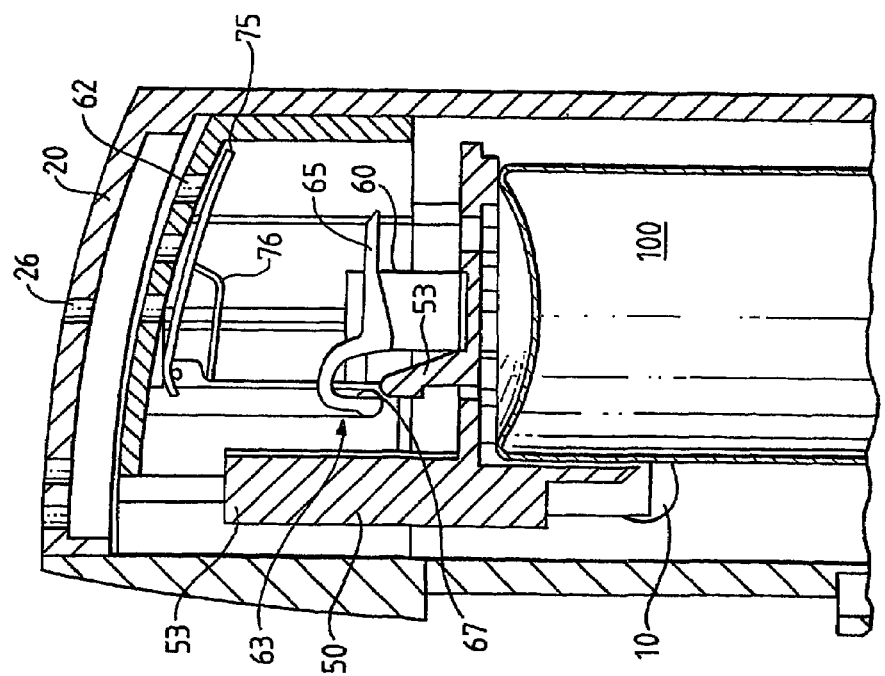

In order to dispense a dose, a user first opens the dust cap 5 by rotating it into a raised position and places the mouthpiece outlet 31 in their mouth and inhales. Inhalation causes a flow of air to be established which passes through the interior of the actuator 1 from the air inlet holes 26 to the mouthpiece outlet 31. As viewed in FIG. 4, this air flow will pivot the vane 74 in a clockwise direction against the bias of the flexible plastic spring 76. Rotation of the vane 74 disengages a distal end 69 of the elongate arm 65 of the slip hook 63 from the end of the vane 74 nearest the pivot point 77 leading to the slip hook 63 rotating in a clockwise direction as shown in FIG. 5 under the pull of the hook 53 on the catch surface 67. Contemporaneously the rotation of the slip hook 63 results in the disengagement of the hook 53 of the canister seat 50 from the catch surface 67 of the slip hook 63. As a result the canister seat 50 is free to move downwardly towards the mouthpiece 4 under action of the leaf spring 60. The canister seat 50 bears against the pressurised dispensing container 100 and movement of the canister seat downwardly thus displaces the pressurised dispensing container 100 towards the mouthpiece 4 resulting in actuation of the internal metering valve of the pressurised dispensing container 100 and dispensation of a dose of medicament out of the pressurised dispensing container through the valve stem block and out of the mouthpiece outlet 31. In this actuated position the ends of the side guide walls 55 come into engagement and rest against the cam surface of the bosses 42 of the dust cap 5.

Figure 6:
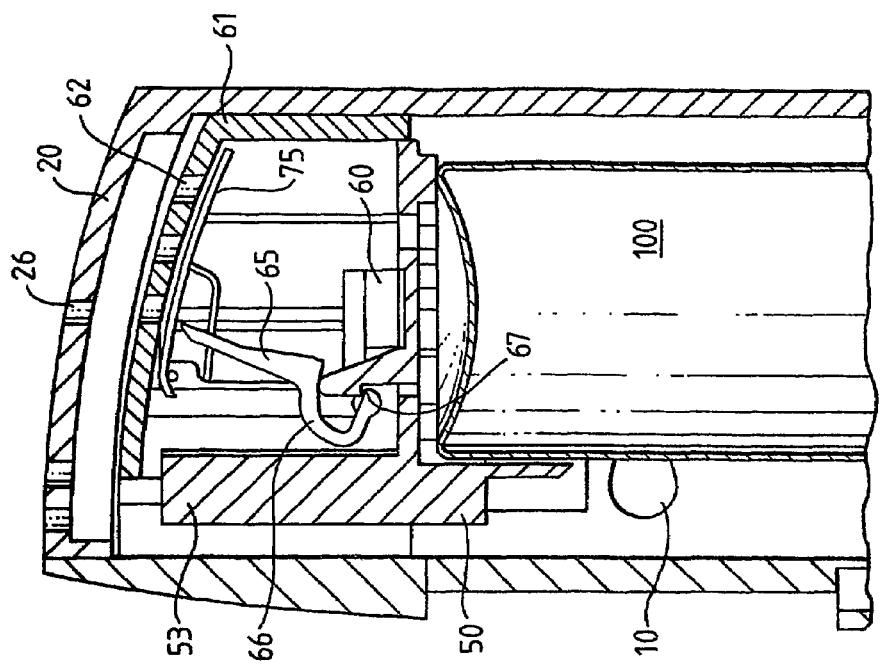

As shown in FIG. 6, the actuator 1 is reset after each dispensation by rotating the dust cap 5 into the closed position wherein the mouthpiece cover 40 covers the mouthpiece 4. Rotation of the dust cap 5 causes the bosses 42 to rotate within the apertures 10. The bosses 42 are engaged with the ends of the side guide walls 55 such that the rotation of the bosses 42 acts to raise the canister seat 50 within the interior of the actuator 1 back into its initial position as shown in FIG. 3. The cam surface of the bosses 42 provides for a degree of over-travel of the canister seat 50 in the upwards direction such that as the canister seat 50 is displaced upwardly the end of the hook 53 contacts the arcuate portion 66 of the slip hook 63 and rotates the slip hook 63 counter-clockwise and then descends slightly to effect re-engagement of the hook 53 with the catch surface 67. The arcuate portion 66 is shaped such that vertical upward movement of the hook 53 smoothly rotates the slip hook 63 counter-clockwise. The upward movement of the canister seat 50 also compresses the leaf spring 60 ready for dispensing of the next dose. As the canister seat 50 moves upwardly within the interior of the actuator 1 the pressurised dispensing container 100 also moves upwardly under the internal spring bias of the metering valve of the container into the ready to dispense position shown in FIG. 3.

FIGS. 7 to 10 illustrate a means for locking and unlocking the actuator 1 in order to lock-out operation of the actuator 1 and a means for inserting and removing a pressurised dispensing container 100 from the housing. As shown in FIG. 7, in a locked state, an upper end 85 of the shoot bolt stem 81 is engaged in the locking aperture 23 on the inside face of the top portion 20 of the rear case 3 preventing separation of the front and rear cases 2, 3. In addition, a distal end of the transverse arm 83 is engaged with an under surface of the vane 74 preventing clockwise rotation thereof and thus preventing operation of the actuator 1. The shoot bolt 80 is displaced upwardly into this position by means of the lock out motor 70 which on operation rotates the lead screw 71 which is engaged with the threaded bore of the shoot bolt stem 81 causing the shoot bolt 80 as a whole to move upwardly within the shoot bolt guide 89 into the locked position of FIG. 7.

Figure 8:
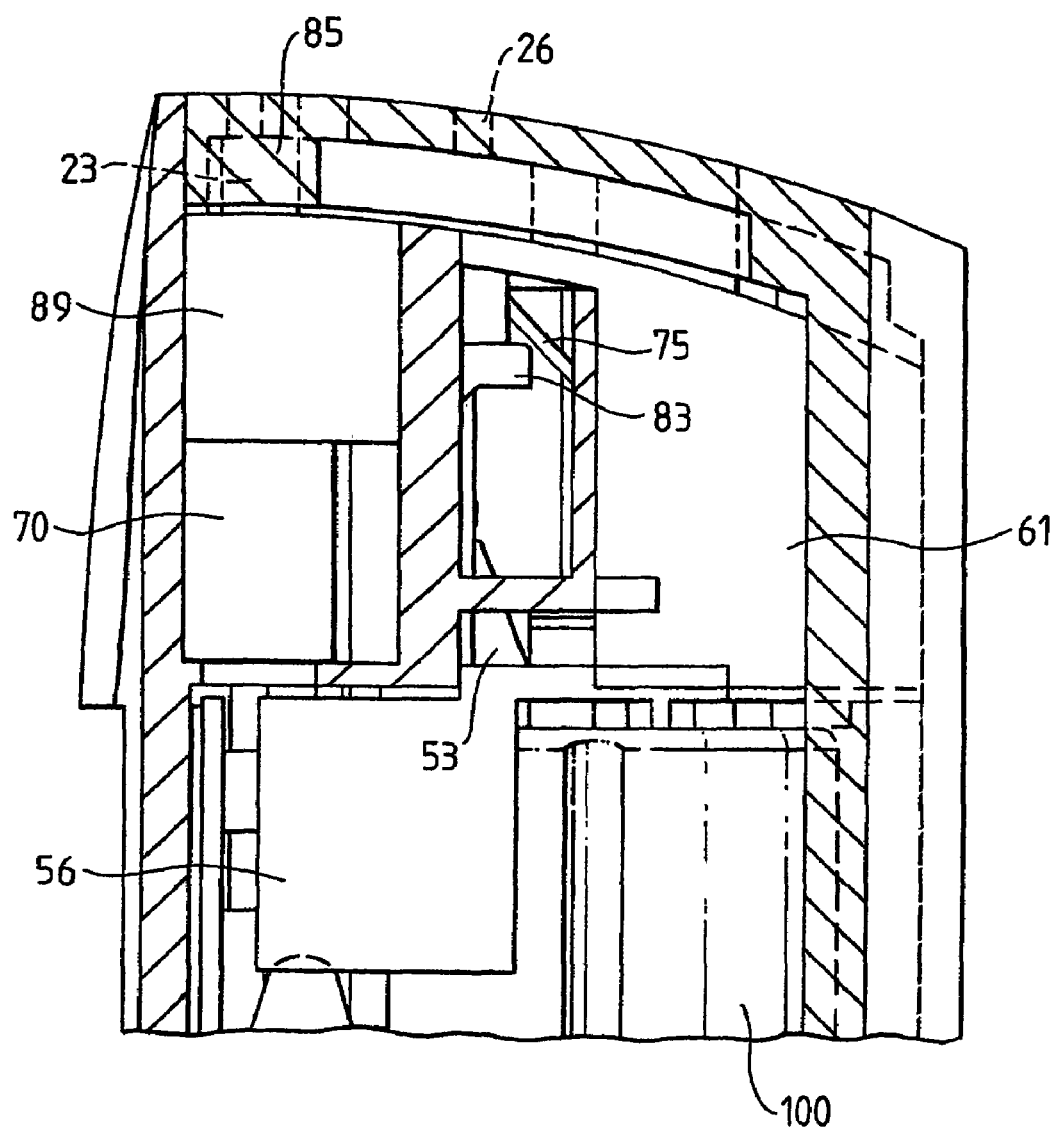

An armed state of the actuator 1 is shown in FIG. 8 in which dispensation of a dose of product as described above may take place but in which the separation of the front and rear cases 2, 3 is still not possible. In this position, the upper end 85 of the shoot bolt stem 81 is still in engagement with the locking recess 23 of the rear case 3 but the shoot bolt 81 has been moved downwardly to a sufficient degree to disengage the distal end of the transverse arm 83 from the vane 74 such that sufficient clockwise rotation of the vane 74 is possible to disengage the hook 53 from the slip hook 63.

Figure 9:
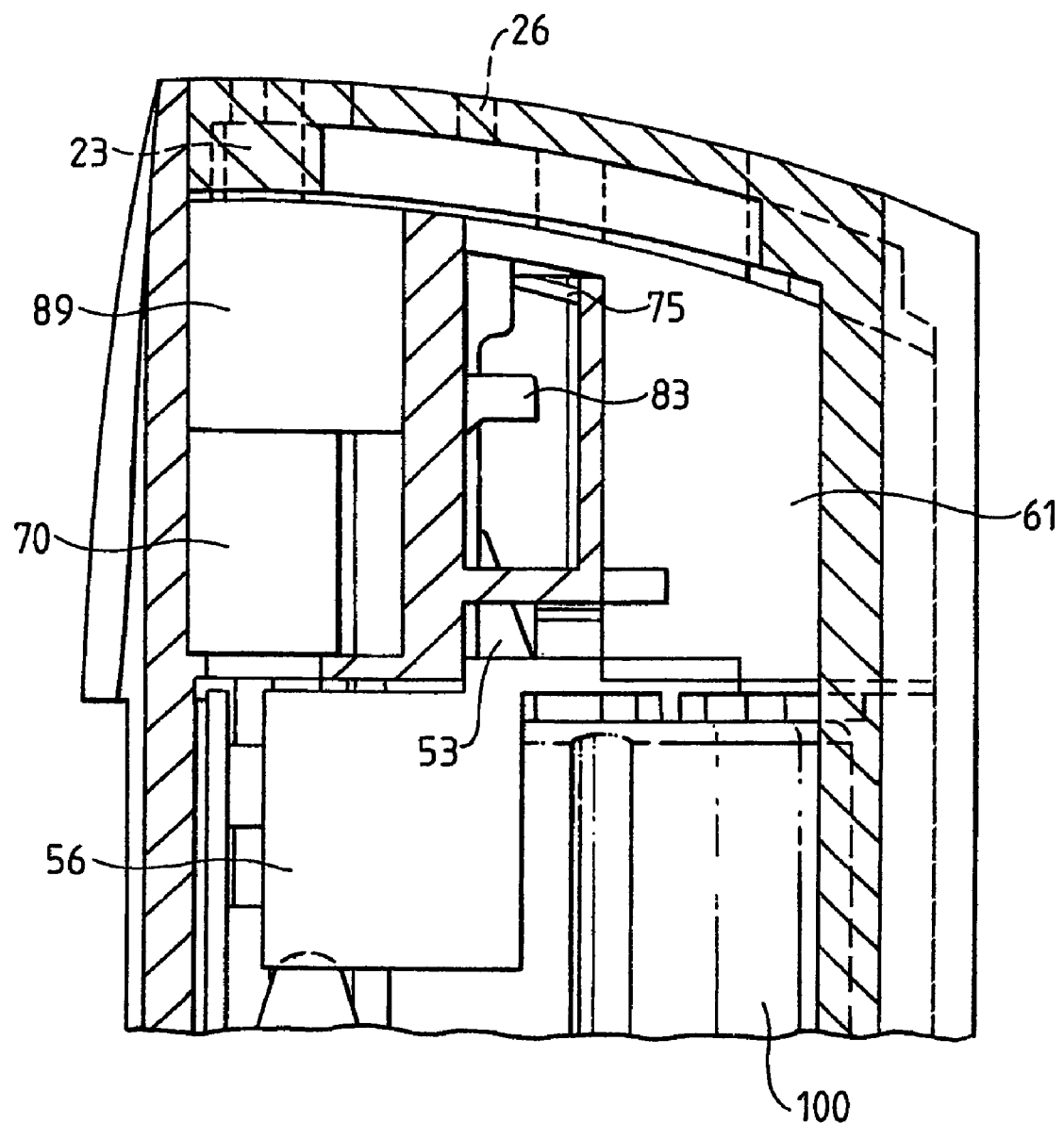
Figure 15:
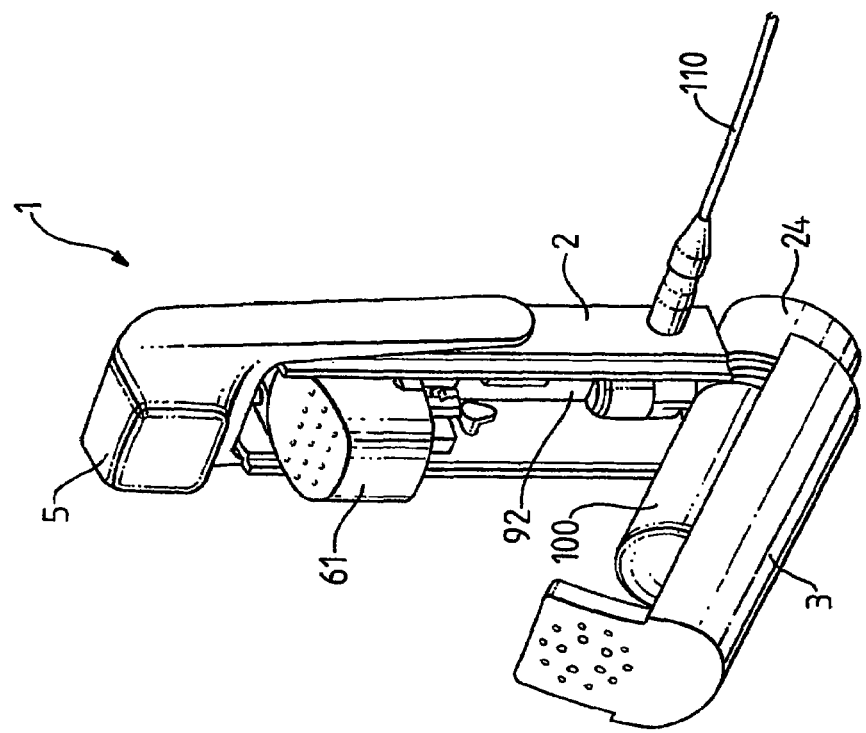

FIG. 9 illustrates an unlocked state of the actuator 1 in which the rear case 3 may be separated from the front case 2. In this state the shoot bolt 80 has been moved further downwards by operation of the lock-out motor 70 to a point where the upper end 85 has been moved out of engagement with the locking recess 23. In this state as shown in FIG. 10, the rear case 3 may be opened by pivoting the rear case 3 relative to the front case 2 about the hinge formed by the hinge portions 13, 22. Movement of the shoot bolt 80 into the armed and unlocked positions described above causes the switch cams 84 on the shoot bolt 80 to operate one or more of the switches 93 on the PCB 6. In this way, the control processor 95 can determine the position of the shoot bolt 80. Advantageously, and as shown in FIG. 15, in the open position, the trigger cap 61 still covers the moving parts of the trigger mechanism 7 preventing damage or tampering therewith. Advantageously, the ability to lock the actuator 1 provides a secure and robust device in which removal of the pressurised dispensing container 100 from the housing is prevented other than by means of excessive force, such as the use of tools.

Preferably, the shoot bolt 80 is only moved from the locked position of FIG. 7 to the armed position of FIG. 8 immediately before a dose is required. Consequently, the device is otherwise in the locked state. As will be described below, the device preferably comprises a security pass code system and it is preferred that the shoot bolt 80 only moves into the armed position after entry of the security pass code.

The lock-out motor 70 advantageously allows for precise movement of the shoot bolt 80. In particular, intermediate positions between the extremes of the shoot bolt's travel are possible, unlike with a solenoid where only 'open' and 'closed' positions are possible. Thus, the shoot bolt 80 and lock-out motor 70 can be used to perform both the functions of locking the housing and locking-out operation of the trigger mechanism 7. In addition, the lock-out motor 70 is a robust mechanism for controlling the shoot bolt 80 which is highly resistant to impact loads, accelerations, and magnetic interference, all of which are known to reduce the effectiveness of solenoids in locking applications. Further, the lock-out motor 70 requires significantly less power to operate than an electromagnetic device such as a solenoid.

Figure 14:
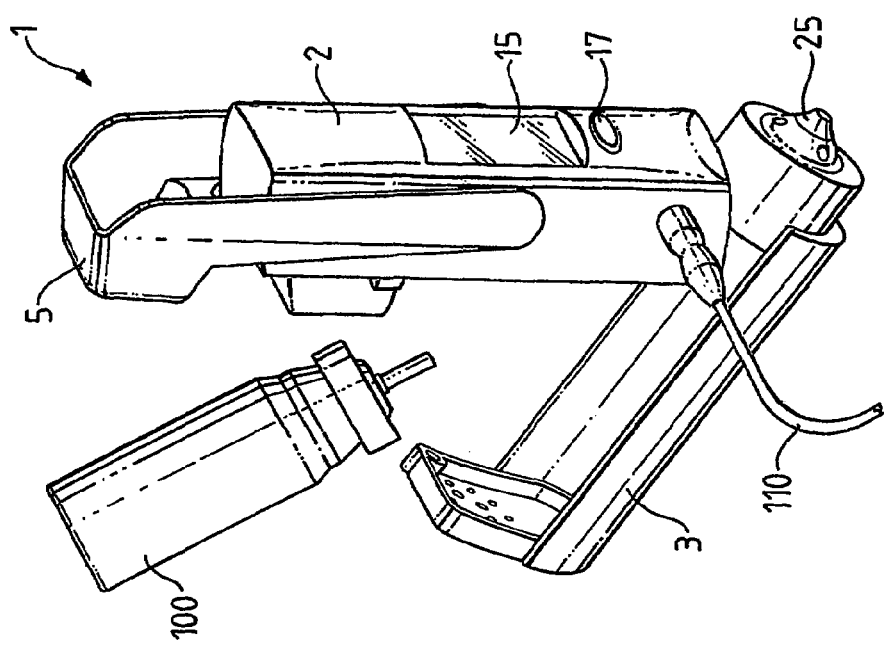

FIGS. 11 to 15 illustrate how the pressurised dispensing container 100 is replaced in practice. From an initial position shown in FIG. 11 the dust cap 5 is first rotated upwardly into the open position as shown in FIG. 12 and the mouthpiece 4 removed by disengaging the socket 34 from the stem portion 24. An interface lead 110 such as a USB cable or an RS232 connector is connected to the data port 14 on the front case 2. An operative connection is established between the control processor 95 of the actuator PCB 92 and an external programming device such as a handheld computer or personal computer (PC). A software program is then run on the external programming device to send and receive instructions and information via the interface lead 110 to/from the control processor 95. In order to remove or insert a pressurised dispensing container 100 the software instructs the control processor 95 to move the shoot bolt 80 downwardly into the unlocked state shown in FIG. 9 wherein the upper end 85 of the stem 81 is disengaged from the locking recess 23. The rear case 3 can then be separated from the front case 2 as shown in FIG. 14 and the pressurised container 100 inserted/removed. The actuator 1 is then closed. The software then instructs the shoot bolt 80 to return to the locked position. The interface lead 110 is then removed. During this insertion/removal procedure, which is preferably carried out by an authorised medical practitioner, and whilst the interface lead 110 is engaged with the data port 14, the control processor 95 may receive instructions from the external programming device to alter the manner of operation of the actuator 1 for subsequent dispense cycles. This can be useful where the product is to be dispensed in a different manner subsequently or where the actuator 1 is to be used by a different user with different prescription requirements. Further, information stored within a memory of the control processor 95 may be downloaded to the external programming device for analysis. This information may relate to matters such as the number and time of doses dispensed by the actuator, the user's compliance with a prescribed dosage pattern, information on errors in operation of the actuator 1, etc. The software run on the external programming device preferably includes instructions for carrying out the above procedures to guide the authorised medical practitioner or other operative.

Figure 17:
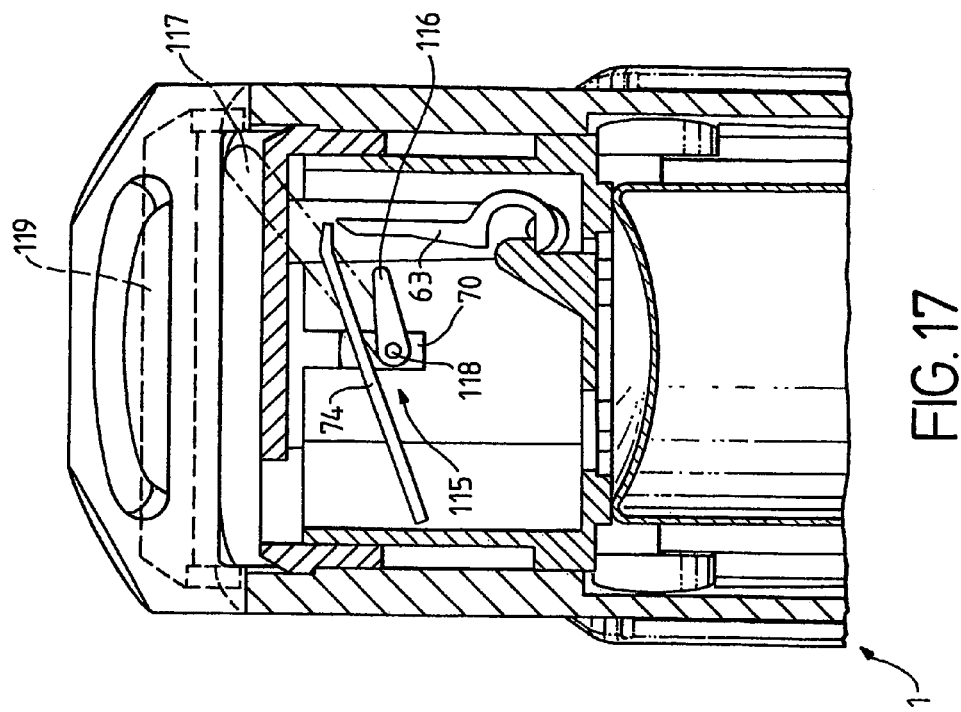
FIGS. 16 and 17 are cross-sectional views of a portion of the device of FIG. 1 showing an alternative mechanism for locking the device.
Figure 16:
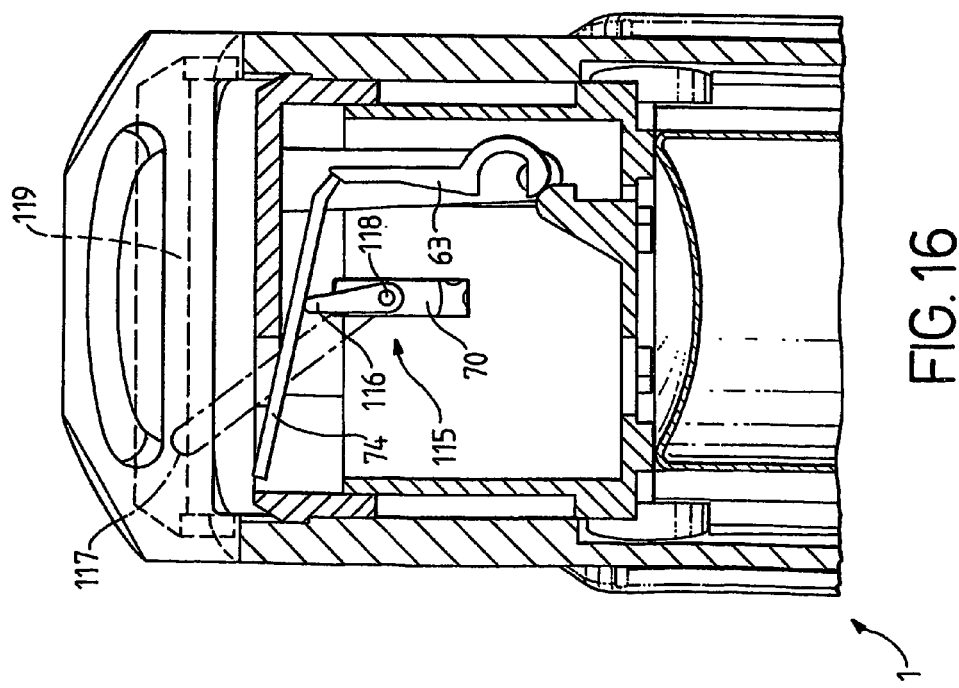

FIGS. 16 and 17 illustrate an alternative mechanism for locking the opening of the front and rear cases 2, 3. Instead of the shoot bolt 80 being used to interface with the rear case 3 and the vane 74, a rotary wiper 115 is provided as shown in FIG. 16. The rotary wiper 115 comprises a vane arm 116 and a lock-out arm 117 each of which depend from a common pivot shaft 118 which is driven to rotate by means of the lock-out motor 70. Preferably, the pivot shaft 118 is itself a rotatable member of the lock-out motor 70. As shown in FIG. 16, the vane arm 116 is rotatable such that a distal end engages an undersurface of the vane 74 to prevent rotation of the vane 74 and thus lock-out operation of the actuator 1. The vane arm 116 may be rotated as shown in FIG. 17, under control of the control processor 95 into a position in which it is disengaged from the vane 74 allowing the vane 74 to rotate on inhalation by a user to cause the vane 74 to disengage from the slip hock 63 allowing dispensation as described above.

The lock-out arm 117 as shown in FIG. 16 is movable into and out of engagement with a locking recess 119. As with the previous embodiment described, engagement of the lock-out arm 117 in the locking recess 119 prevents separation of the front and rear cases 2, 3.

Figure 18:
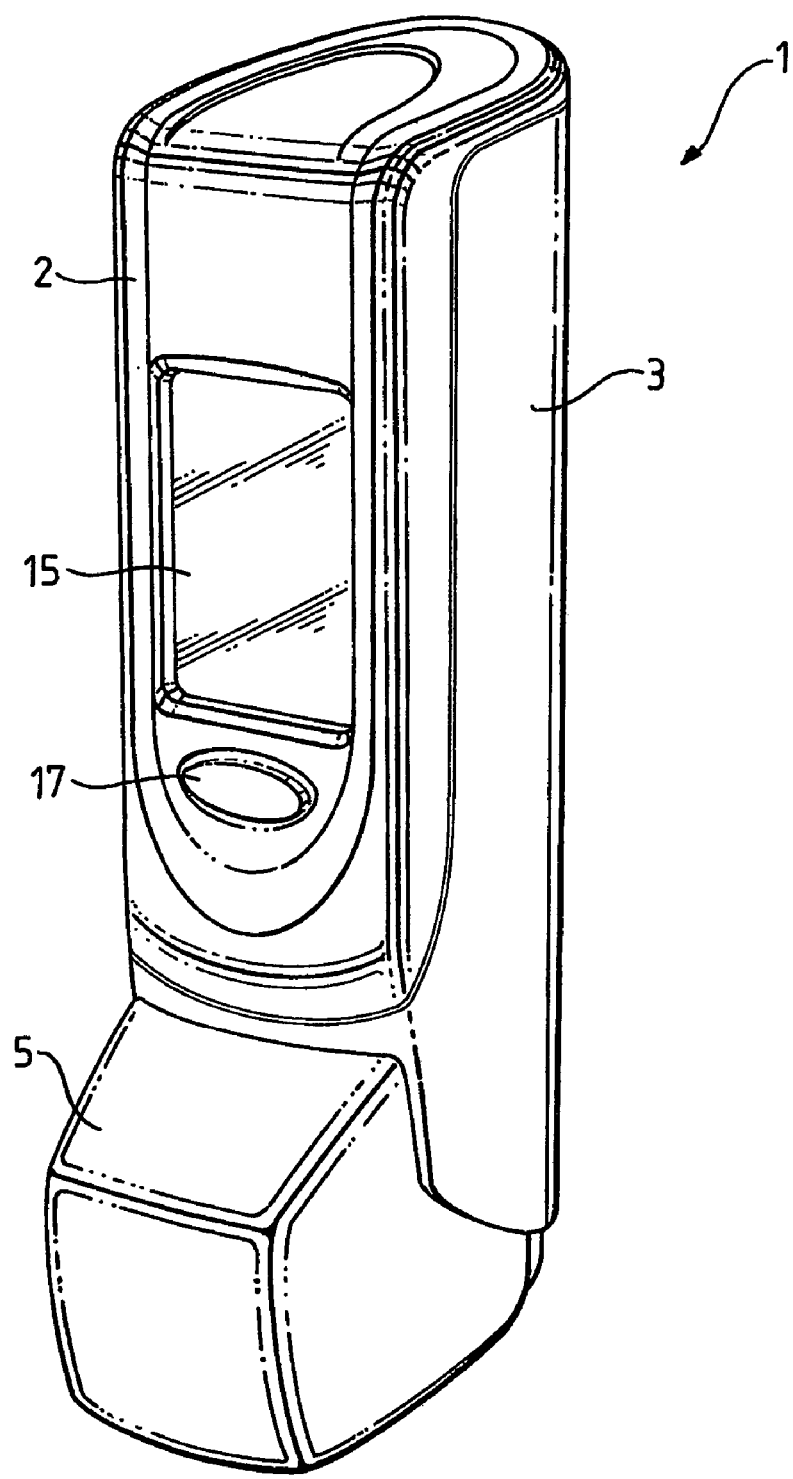
FIG. 18 is a perspective view of a second embodiment of dispensing device according to the present invention.
Figure 19:
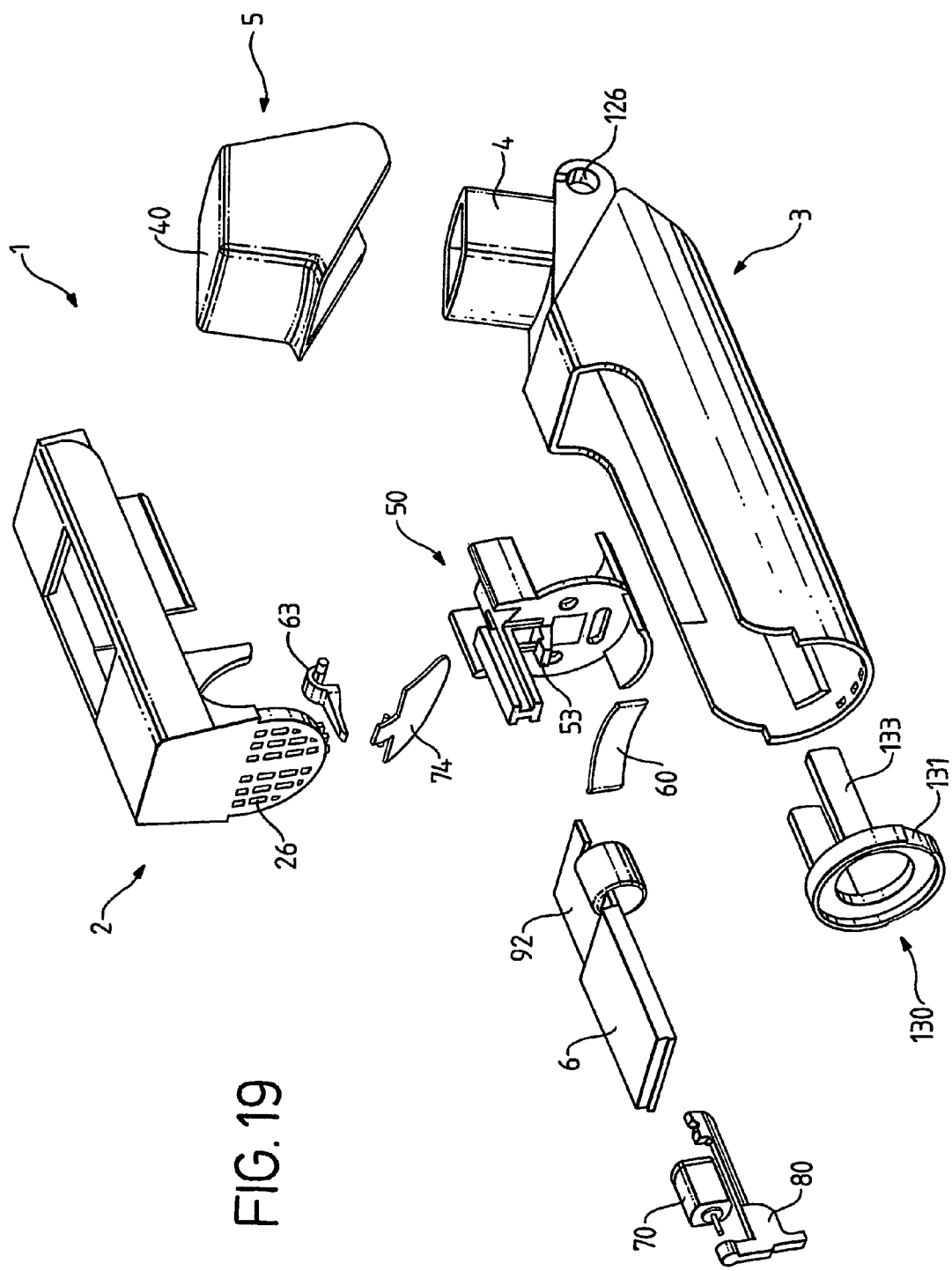
FIGS. 19 and 20 are perspective exploded views of the device of FIG. 18.
Figure 20:
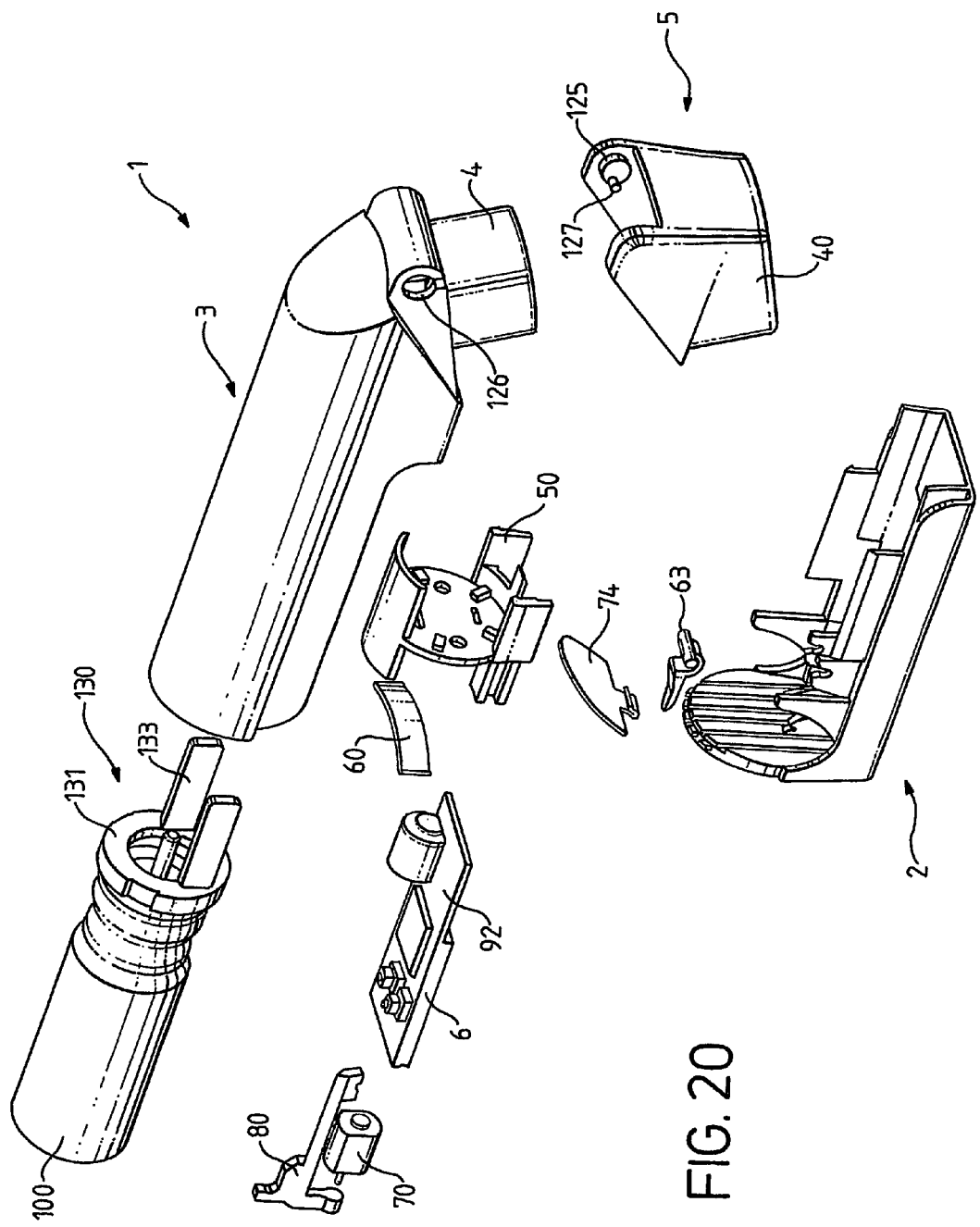

A second embodiment of dispensing according to the present invention is shown in FIGS. 18 to 20. This embodiment is particularly suitable for a disposable device where it is not intended to replace the pressurized dispensing container 100 after it has been emptied. Many of the components of the second embodiment are the same or similar to those described above with reference to the first embodiment. Like reference numerals have been used for like components and common features will not be discussed in further detail.

As shown in FIG. 18, the actuator 1 again comprises a front case 2, rear case 3, mouthpiece 4 and dust cap 5. In the second embodiment the mouthpiece 4 is not formed as a separate removable component but integrally with the rear case 3. The dust cap 5 is also simplified compared to the first embodiment and comprises a mouthpiece cover portion 40 which is pivoted to the rear case 3 by means of engagement of bosses 125 in apertures 126 formed at the mouthpiece end of the rear case 3 as shown in FIGS. 19 and 20. Each boss 125 is provided with an eccentrically positioned peg 127, although a cam surface may alternatively be used as described above with reference to the first embodiment.

As shown in FIG. 20, the actuator 1 comprises a canister seat 50, leaf spring 60, PCB 92, shoot bolt 80, slip hook 63 and lock-out motor 70. In addition, the actuator comprises a canister reset seat 130 which is engaged against the valve stem end of the pressurised dispensing container 100 in use. The canister reset seat 130 comprises an annular member 131 which engages a ferrule 132 of the pressurized dispensing container 100 and two elongate arms 133 which extend from the annular member 131 towards the mouthpiece 4.

Operation of the second embodiment of actuator 1 to dispense a dose of medicament is similar to that described above with reference to the first embodiment. On actuation, the distal ends of the elongate arm 133 move downwardly within the interior of the actuator 1 to come to rest against the pegs 127 of the bosses 125 of the dust cap 5. In addition, means for locking operation of the actuator 1 and separation of the front case 2 and rear case 3 may be provided as described above with reference to the first embodiment. However, the means for resetting the actuator 1 after each dispensation is different from that described above. In the second embodiment, resetting of the device is again achieved by rotation of the dust cap 5. Rotation of the dust cap 5 from the open position into the closed position in which it covers the mouthpiece 4 causes the bosses 125 to rotate within the apertures 126 of the rear case 3. Consequently, the pegs 127 on the bosses 125 are moved from a lower position within the rear case 3 to an upper position. As the pegs 127 are engaged against the distal ends of the elongate arms 133 of the canister reset seat 130, rotation of the dust cap 5 causes the canister reset seat 130 and consequently the pressurized dispensing container 100 to be moved upwardly within the interior of the actuator 1 against the bias of the leaf spring 12 to re-engage the hook 53 of the canister seat 50 with the catch surface 67 of the slip hook 63.

In other respects the second embodiment of actuator 1 operates in the same manner as described above with reference to the first embodiment.

Figure 21:
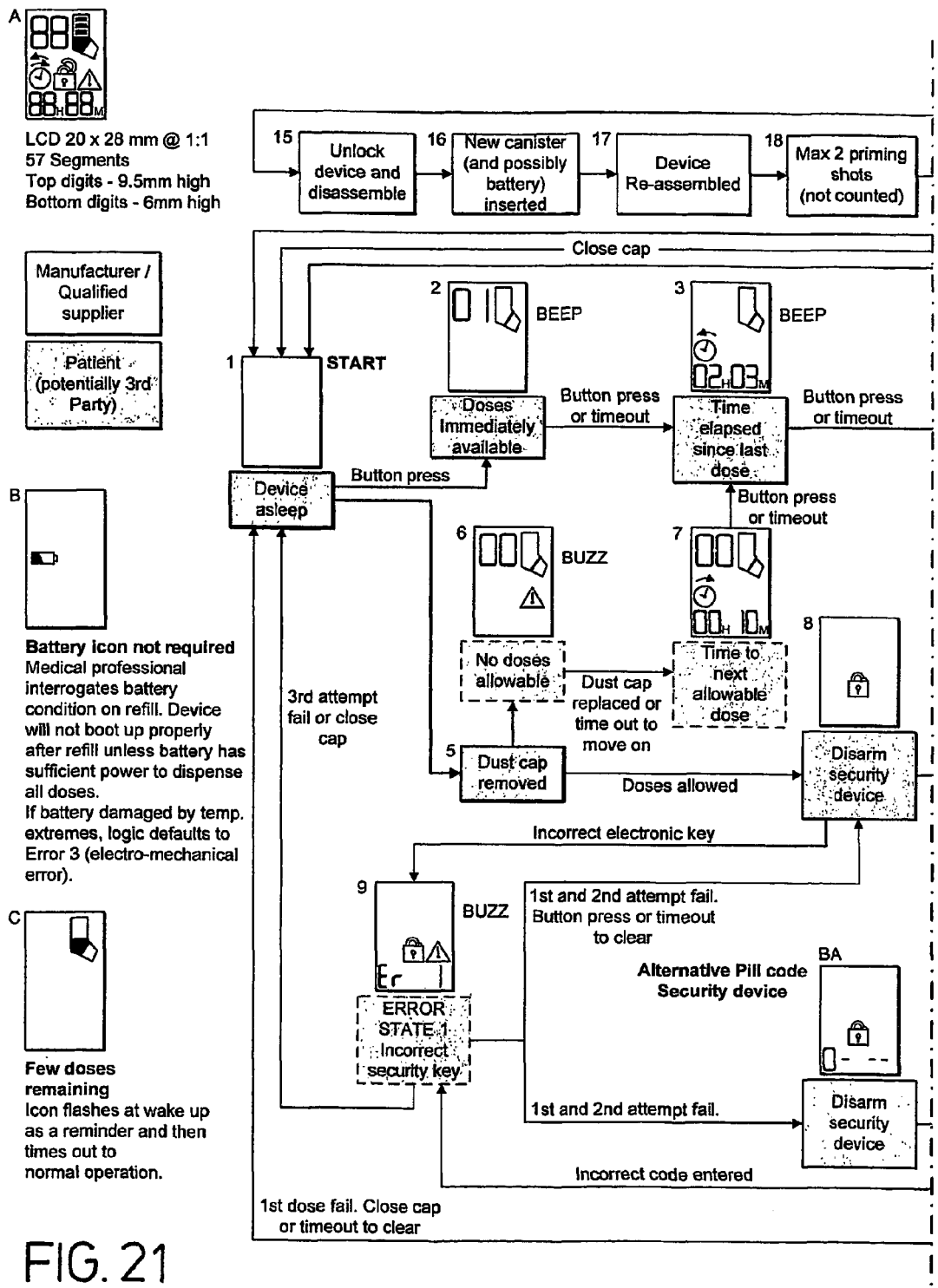
FIG. 21 is a schematic illustration of a user interface for use with embodiments of dispensing device of the present invention.
Figure 21:
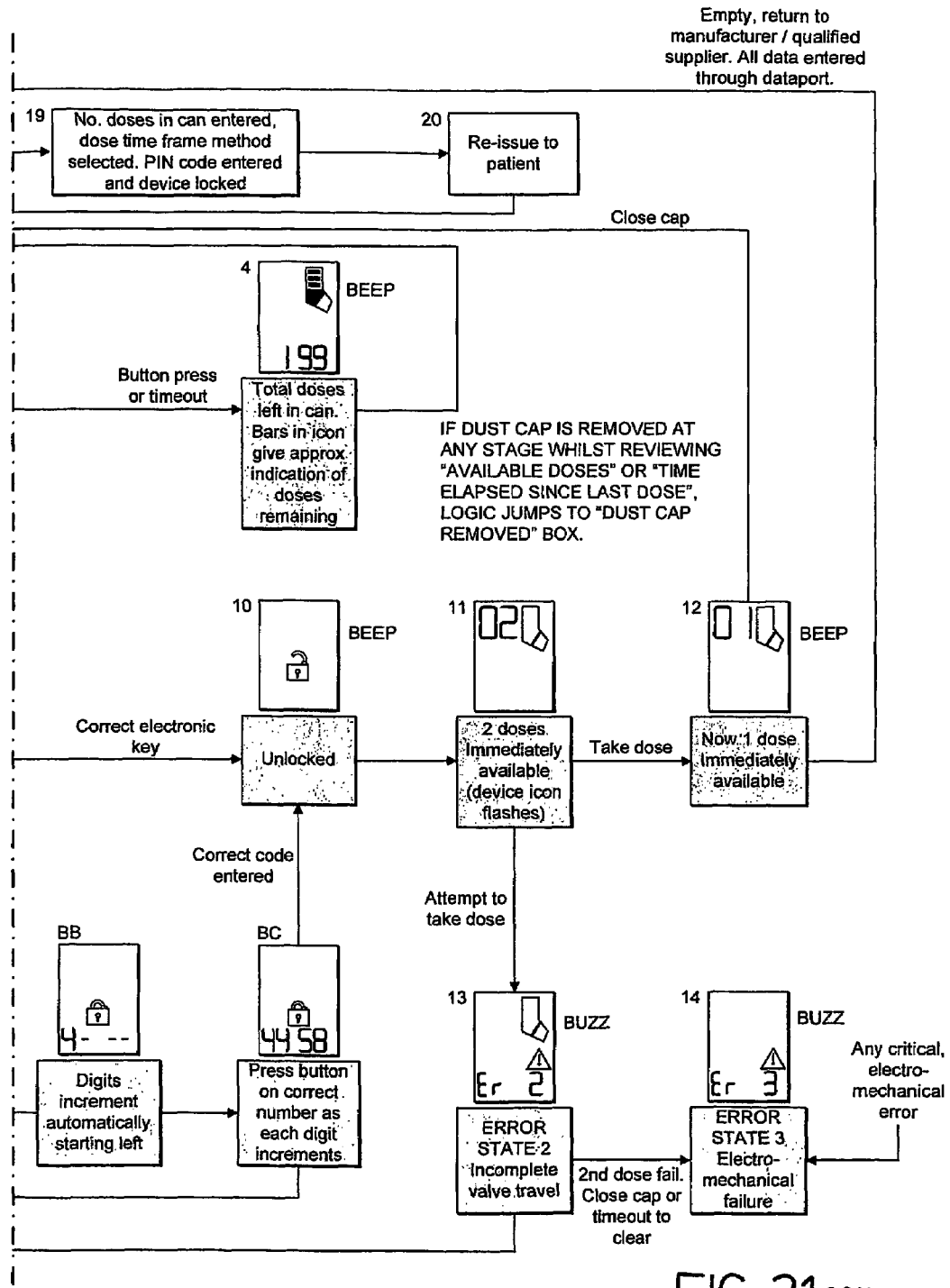

FIG. 21 illustrates schematically a user interface displayed on the LCD screen 15 of the actuator 1 and accessed and navigated through by the operating button 17. Advantageously, the user interface is operated and navigated by using only one operating button 17. The LCD screen 15 comprises a plurality of icons 135 and alphanumeric character blocks 136 as shown in Box A which may be illuminated in varying combinations to display topical information to the user of the actuator 1. The LCD screen 15 appears blank as shown in Box 1 in a standby mode where, for example, the actuator 1 has not been used for some time. If the operating button 17 is depressed with the dust cap 5 in the closed position the LCD screen 15 illuminates to display the number of doses immediately available for dispensing shown in Box 2. The LCD screen 15 preferably then proceeds either at fixed time intervals or on further depressions of the operating button 17 to display the time elapsed since the last dose, as shown in Box 3, and then the total number of doses remaining in the pressurized dispensing container 100, as shown in Box 4. The LCD screen 15 then returns to the standby display of Box 1.

From the standby mode, if the dust cap 5 is opened the LCD screen 15 displays one of two screens dependent on the state of the actuator 1. If no dose is currently available because, for example, the user has recently taken a previous dose and is not yet permitted to take a further dose, Box 6 is displayed indicating a warning to the user followed by the, display of Box 7 indicating the time remaining until the next dose can be dispensed. The display may then return the standby mode of Box 1 or proceed to the displays of Boxes 3 and 4 to indicate the time elapsed since the last dose and total number of doses left in the pressurized dispensing container 100. Alternatively, if on opening of the dust cap 5, a dose is available for immediate dispensation Box 8 is displayed indicating that a pass code is required to be entered by the user before dispensation can take place. If the correct pass code is entered by the user the display moves to Box 10 indicating that the actuator 1 is unlocked and it then proceeds to display Box 11 indicating the number of doses that can be dispensed immediately, in this example '2'. Once a dose has been taken by a user in the manner described above, the display decrements the number of doses immediately available to '1' as shown in Box 12. The user at this point must close the dust cap 5 in order to reset the device as described above. At this point the LCD screen 15 returns to the standby display of Box 1. Alternatively, if on taking a dose the actuator 1 determines that the pressurized dispensing container 100 is empty this information is displayed to the user and the actuator 1 must be returned to an authorised medical practitioner for refilling.

One method of inputting the pass code is illustrated in Boxes 8A to 8C. A three or four digit alphanumeric code is entered one digit at a time. To allow operation by a single operating button 17 the display as shown in Box 8A automatically cycles through the potential alphanumeric characters for the first digit. The user then presses the operating button 17 when the correct alphanumeric character for the first digit is displayed as shown in Box 8B. The display then cycles through the available alphanumeric characters for the second digit and so on until the complete code has been entered as shown in Box 8C.

An alternative method for inputting the pass code involves the user themselves cycling through the potential alphanumeric characters. In this method each press of the operating button 17 changes the character displayed, initially for the first digit. Once the correct character is displayed the user presses and holds for a fixed period, such as a second, the operating button 17 to confirm the selection and to move onto the second digit, and so on until the entire code has been entered.

If at any point an incorrect code is entered, the display illuminates as shown in Box 9 to indicate that an error has occurred. Preferably two or three attempts are allowed for the user to input the correct pass code. If after a predetermined number of attempts the correct pass code has still not been entered then the actuator 1 remains locked and the display moves to the standby state of Box 1.

The LCD display 15 is also able to display other information in connection with operation of the actuator 1. In particular, as shown in Box 13 the display can illuminate to indicate if operation of the pressurized dispensing container 100 during a dose dispensation was ineffective due to, for example, incomplete valve travel. The display may also be capable of showing a general failure display as shown in Box 14 where the internal components of the actuator 1 have suffered an electromechanical failure such as, for example, failure of the lock-out motor 70.

As shown in Box B, the display 15 may indicate if the internal battery of the PCB 92 is close to exhaustion, although this information preferably is only displayed to an authorised medical practitioner on inserting a pressurized dispensing container 100. Preferably, the software in the actuator 1 and the external programming device is able to determine whether the battery 94 has sufficient power to dispense all doses contained in the pressurized dispensing container 100. The determination may be made by interrogating the battery 94 to ascertain its remaining power or by logging and analysing the accumulated usage of the battery 94, or by a combination of these methods. Where logging of accumulated usage is chosen the memory of the control processor 95 can be used to store information on the number of actuations of the lock-out motor 70 and/or the total time the LCD display 15 has been powered on. This information can then be used to work out the remaining power in the battery 94 since the initial power capacity or rating of the battery 94 is known.

As shown in Box C, the display 15 may display an icon, preferably in a flashing mode, to indicate if the pressurized dispensing container 100 is low on remaining doses.

The visual displays of the LCD screen 15 may also be accompanied or replaced by audio signals such as buzzes, beeps or combinations thereof, or tactile signals such as vibrations to alert a user to the status of the device.

The control processor 95 and LCD display 15 may together be used to control operation of the actuator by regulating the number of actuations in a particular time period and/or the time interval between individual actuations. In one version the control processor 95 may be programmed to allow a predetermined number of actuations to be taken during a 'rolling' time interval. For example, three actuations may be allowed during any 24 hour period. Thus the 'rolling' window of 24 hours starts when the first actuation takes place. Thereafter two further actuations are possible within 24 hours. In other words, a fourth actuation is not possible until 24 hours after the first actuation. The window is a 'rolling' window in that a fifth actuation is not possible until 24 hours after the second actuation, a sixth actuation is not possible until 24 hours after the third actuation, and so on. By using a rolling time frame the device prevents a user taking too many doses at a transition point between fixed time frames. For example, the user is prevented from taking three doses near the end of a first 24 hour period and three further doses near the start of a second, successive 24 hour time period which would lead to six doses being administered in under 24 hours. An advantage of the described operating system is that the exact timing of each actuation within the 24 hour period can be decided by the user. This is an advantage for medicaments that have an accumulative effect on a user whereby the exact timing of each dose is less critical than the total quantity of medicament dispensed over a particular time period. By allowing a user to determine themselves when they take the doses in that period the actuator 1 allows for a flexible dispensation pattern which is more suited to a user's needs. The number of possible doses in each time period and the length of the time period can be varied as required by the prescription requirements of each individual user and the figures given above are merely exemplary.

In another version, the control processor 95 may be programmed to allow actuations to take place only after a minimum time interval of, for example, 4 hours. This mode of operation may be used separately from the 'rolling' window described above or in combination. Thus in combination, the control processor 95 may flexibly allow a user to take, say, 3 actuations within any 24 hours and at the same time ensure that no two doses are taken within, say, 1 hour of each other. This advantageously provides a great deal of flexibility and control of the prescription regime.

In another version, the control processor 95 is provided with clock running on either an internal time or a real time basis. The control processor 95 is programmed to allow a set number of doses to be administered each 'day' or other fixed time interval determined by the clock. Thus the timing of the doses is determined by an absolute time measure rather than a relative time measure dependant on the timing of previous doses. This mode of operation is advantageous for medicaments which are prescribed at fixed intervals which may be one or more days apart. A real time clock may also be used to ensure that a medicament is not used after the expiry date has passed. The expiry date information may be input to the control processor by the external programming device on insertion of the pressurised dispensing container.

The control processor 95 may also be used to prompt a user to take a dose at a particular time. The prompt may take the form of a visible signal on the LCD 15, an audible alert, a tactile alert such as a vibration, or a combination of the above. The prompt can be used to assist a user's prescription regime by reminding the user to take a dose at the 'best' time. However, this prompting system may be combined with the operating modes described above. Thus the device may use a 'rolling' window mode to allow flexibility in the timing of doses within a time period but still recommend to a user that the doses are taken at specific times.

FIGS. 22 to 31 illustrate a mechanism which may be incorporated into either of the embodiments of actuator 1 described above for automatically removing the actuating force from the pressurized dispensing container 100 after dispensation of a dose of medicament. This is useful in overcoming a potential problem with the unmodified embodiments described above which may occur if the dust cap 5 is left in the open position after dispensation of a dose. In the unmodified embodiments described above, the biasing force of the leaf spring 60 continues to act via the canister seat 50 on the pressurized dispensing container 100 and maintains the pressurized dispensing container 100 in the depressed state with the internal metering valve of the pressurized dispensing container 100 in an actuated position. Whilst the internal metering valve contains seals to isolate the bulk product from the exterior of the pressurized dispensing container 100 in the actuated position, it is known that over time these seals may be subject to leakage of medicament and/or pressurized gas. As a result, it is advantageous that the mechanism of the present invention described below enables the biasing force to be automatically removed from the pressurized dispensing container 100 even where the dust cap 5 is left in the open position.

Figure 22:
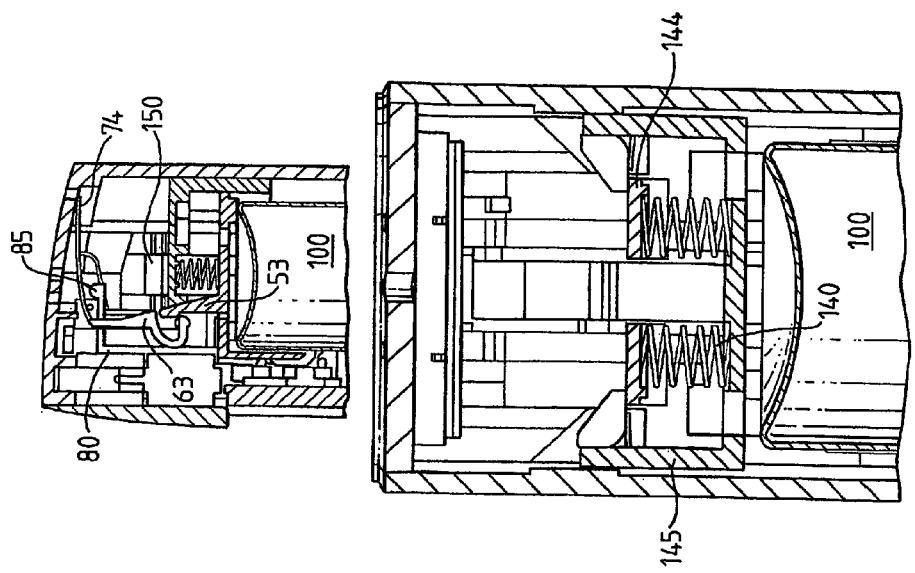
FIGS. 22 to 31 are cross-sectional views through a portion of a third embodiment of dispensing device according to the present invention illustrating a typical dispensing and re-setting cycle.
Figure 35:
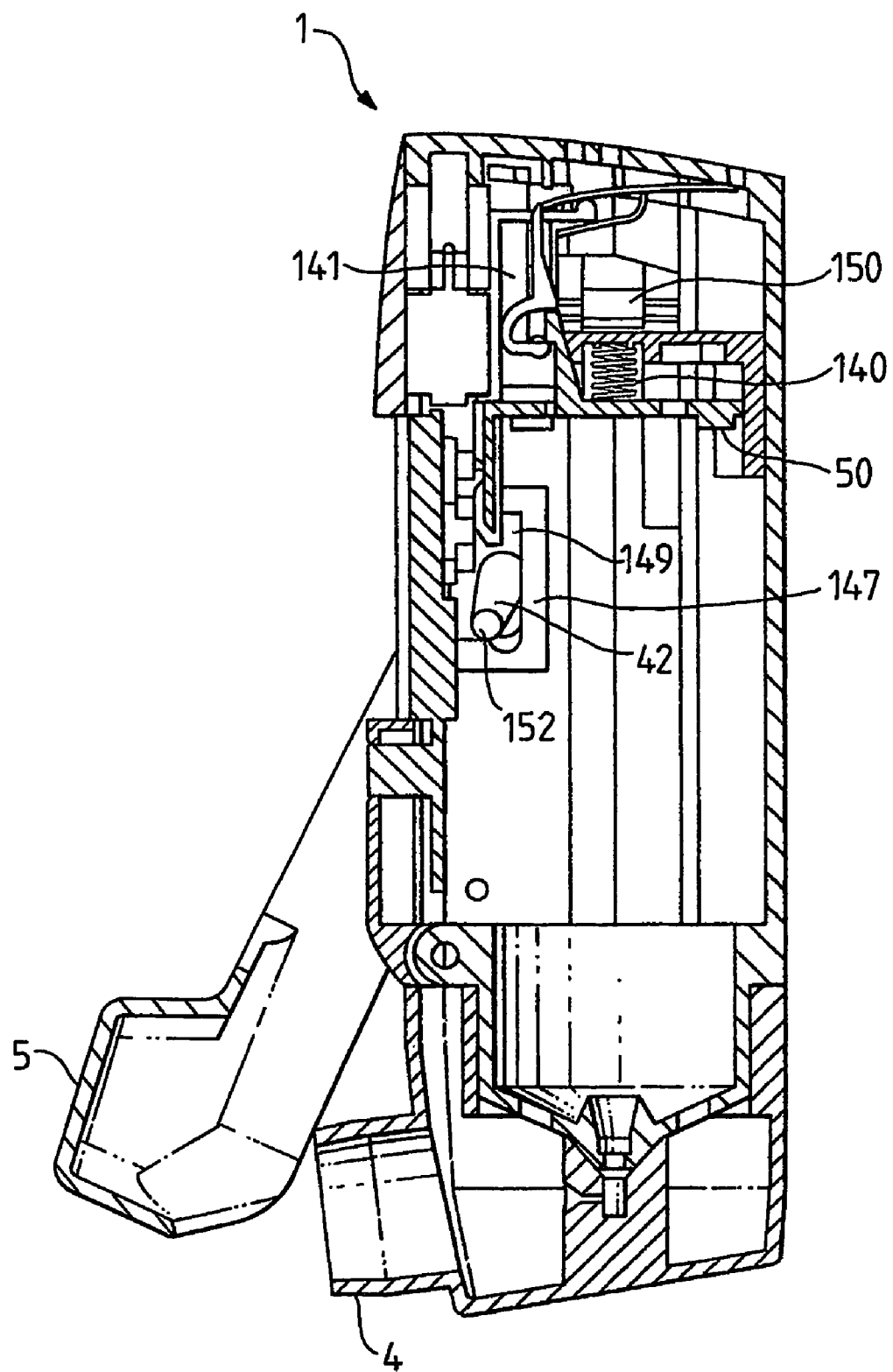
Figure 36:
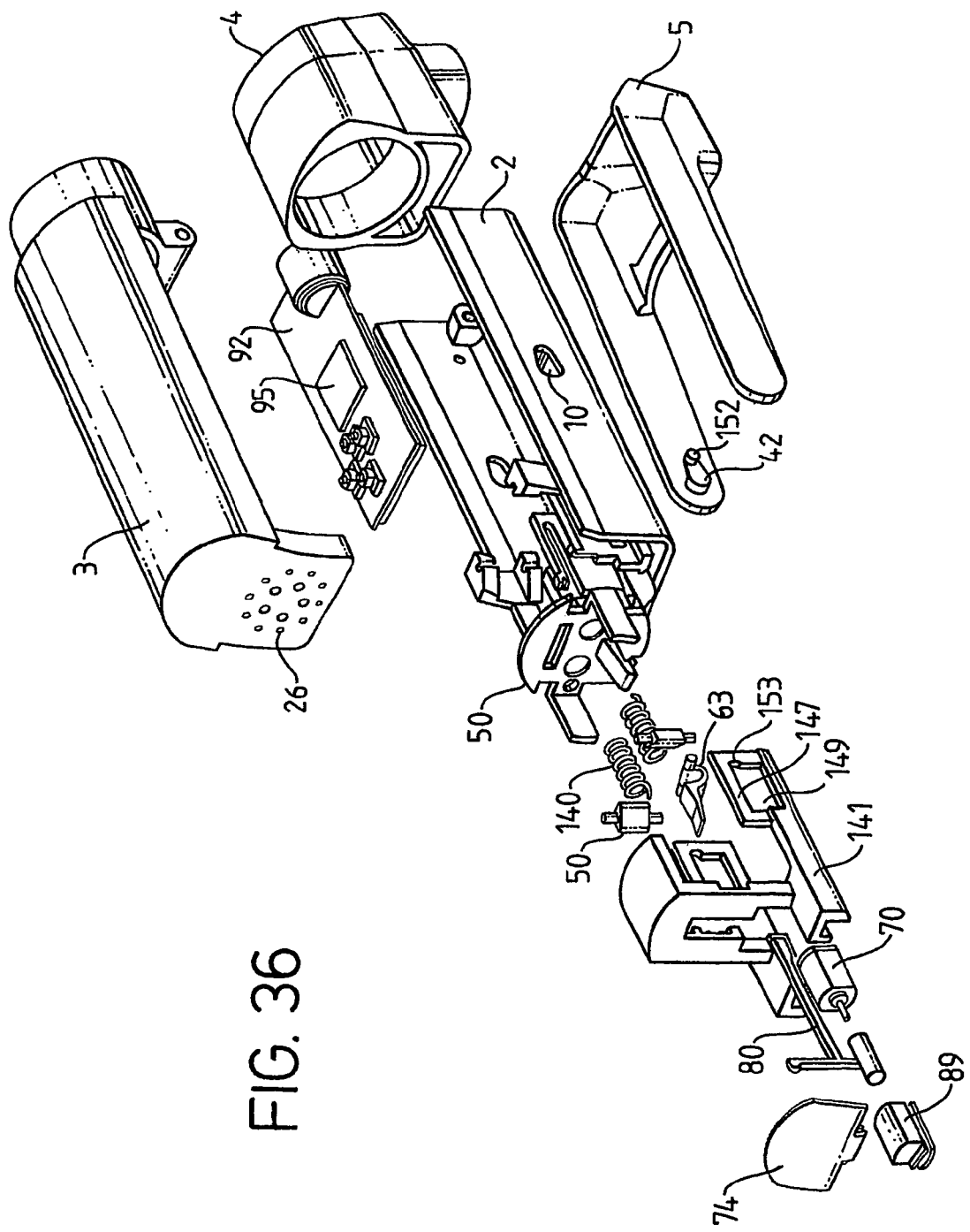
FIG. 36 is an exploded perspective view of the device of FIGS. 22 to 31.

As shown in FIGS. 22 to 36, the mechanism for removing the biasing force from the pressurized dispensing container 100 comprises a modified canister seat 50, two helical springs 140 instead of the leaf spring 60 and additional components in the form of a retainer member 141 and a pair of toggles 150. As shown in FIGS. 22 and 36, the modified canister seat 50 comprises two upstanding guide arms 145 which are diametrically opposed to one another. The retainer member 141 is received in the interior of the actuator 1 and is slidable relative to the modified canister seat 50. The pair of helical springs 140 span between the modified canister seat 50 and two springs seats 142 provided on an undersurface of a transverse platform 144 of the retainer member 141. An upper surface of the transverse platform 144 forms two toggle catch surfaces 143, the use of which will be described below.

The pair of toggles 150 are pivotally mounted to the chassis 16 of the actuator 1. Initially, with the mechanism in a position ready for dispensation of a dose of medicament as shown in FIG. 22 rotation of the toggles 150 due to the bias of the helical springs 140 is prevented by contact with the guide arms 145 of the modified canister seat 50.

In the position of FIG. 22 the helical springs 140 are compressed between the retainer member 141 and the modified canister seat 50. The toggles 150 are engaged with the toggle catch surfaces 143 of the retainer member 141 preventing upward movement of the retainer member 141 away from the modified canister seat 50. Downward movement of the canister seat 50 and pressurized dispensing container 100 is prevented as described above by engagement of the hook 53 with the slip hook 63. In addition, as shown in FIG. 22 the shoot bolt 80 is in the locked position with the transverse arm 83 contacting the vane 74 preventing actuation of the actuator 1.

Figure 23:
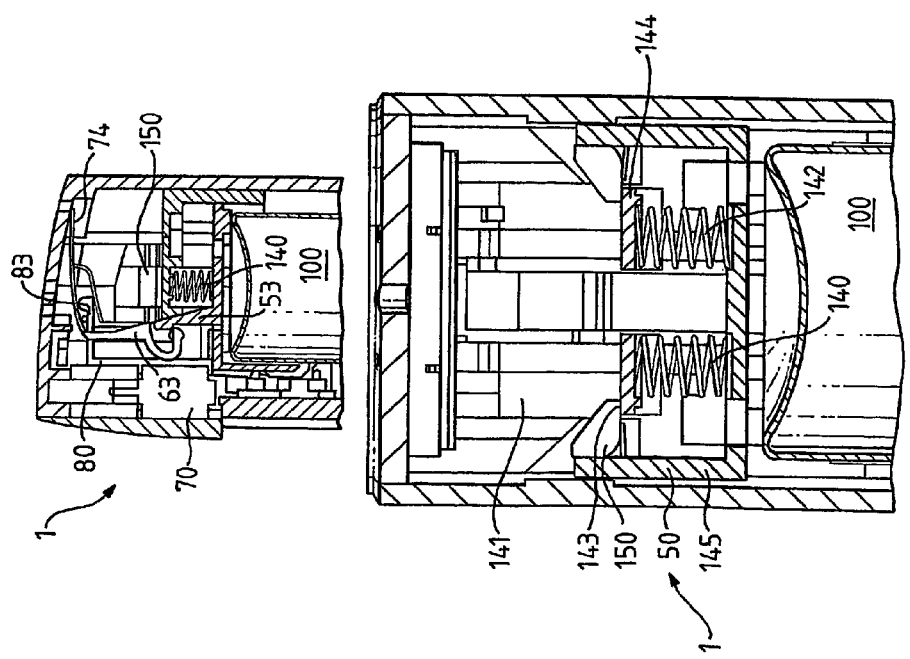

FIG. 23 shows the trigger mechanism in the unlocked state with the transverse arm 83 out of engagement with the vane 74. At this point the positions of the retainer member 141, toggles 150 and modified canister seat 50 are unchanged.

Figure 25:
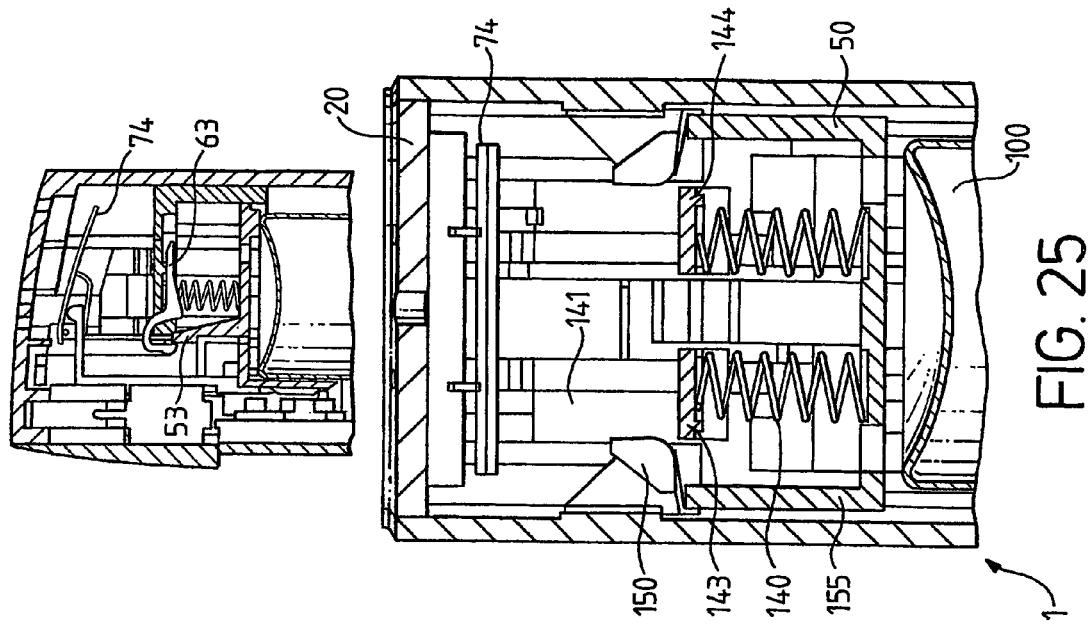
Figure 24:
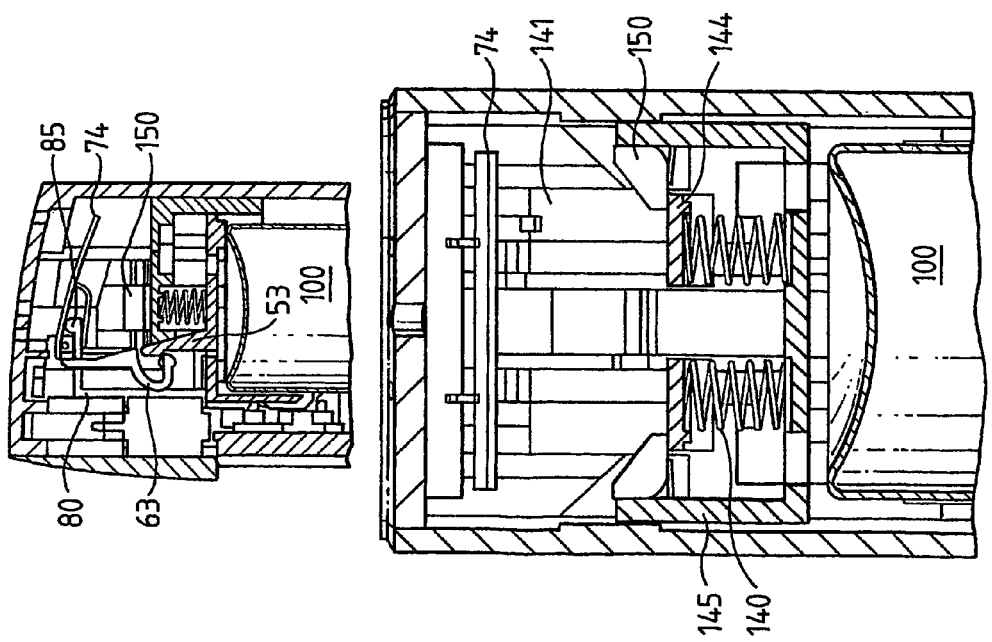
Figure 26:
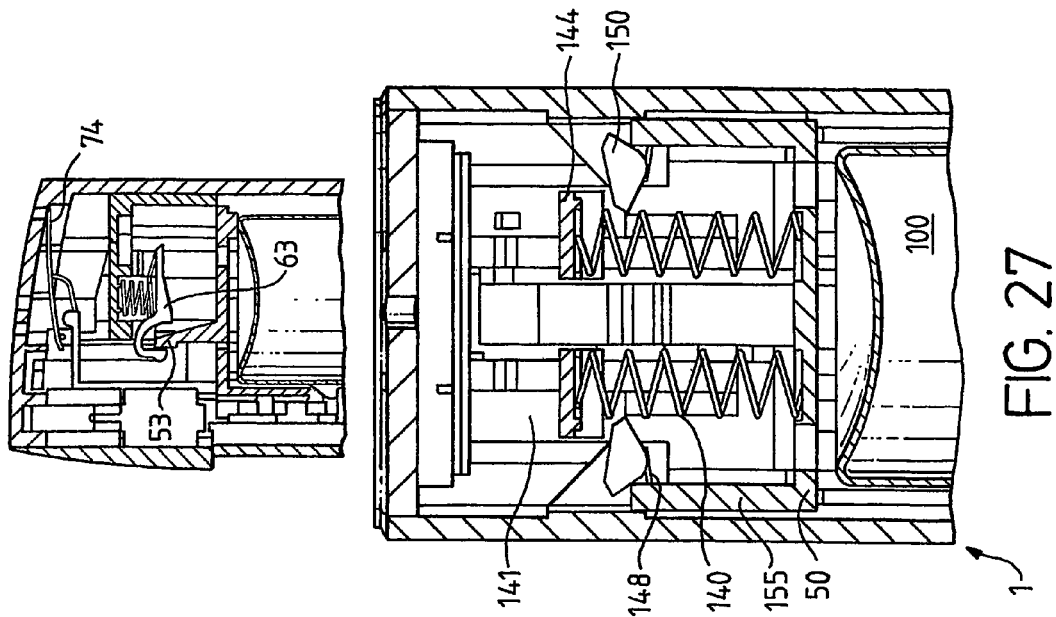
Figure 27:
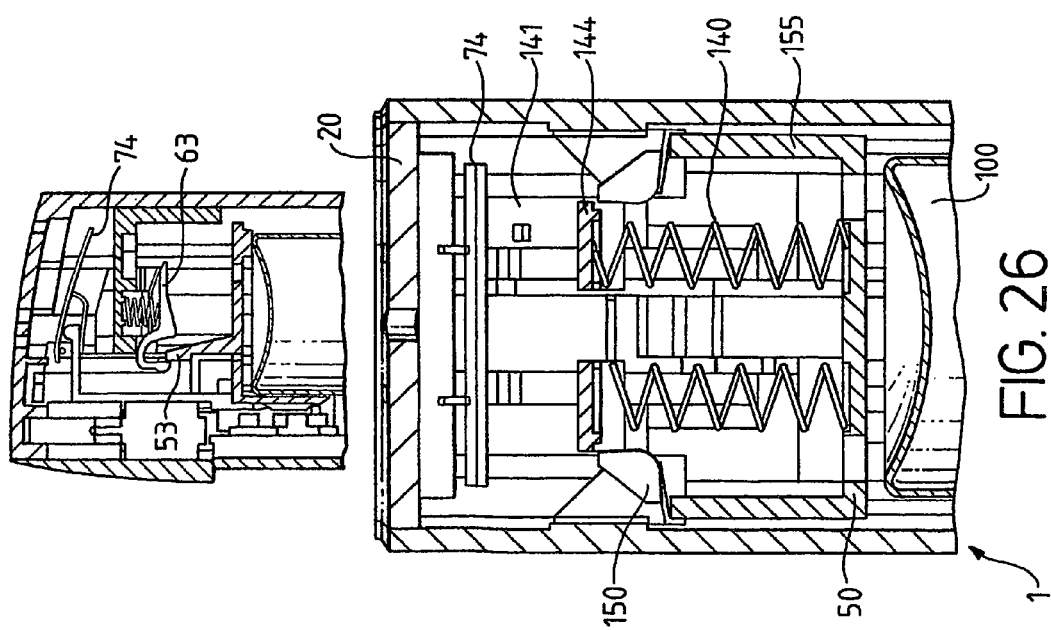
Figure 28:
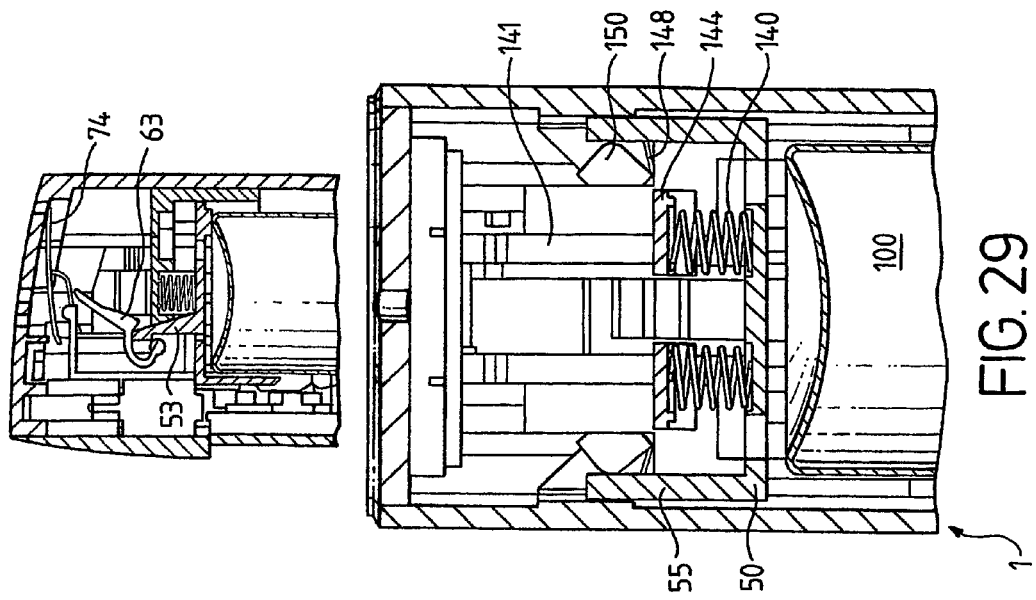

FIG. 24 shows the point when inhalation by a user has commenced causing the vane 74 to rotate in a clockwise direction leading to disengagement of the vane 74 from the distal end 69 of the elongate arm 65 of the slip hook 63. Consequently, as shown in FIG. 25, the hook 53 disengages from the catch surface 67 of the slip hook 63 and the modified canister seat 50 and the pressurised dispensing container 100 are displaced downwardly towards the mouthpiece 4 in order to dispense a dose of medicament as described previously. Contemporaneously the downward movement of the modified canister seat 50 moves the guide arms 155 of the modified canister seat 50 out of engagement with the outer faces of the toggles 150 as shown in FIG. 25. Consequently, the toggles 150 are free to rotate under the bias of the helical springs 140 acting through the modified canister seat 50 into the position shown in FIG. 25 wherein the toggles 150 have moved out of engagement with the toggle catch surfaces 143 of the retainer member 141. As a result, the retainer member 141 is free to move upwardly within the actuator 1 towards the top portion 20 of the rear case 3 under action of the helical springs 140 with the transverse platform 144 passing in between the two toggles 150 as shown in FIG. 26. As the retainer member 141 moves upwardly, the transverse platform 144 clears the toggles as shown in FIG. 27. At the same time, movement of the retainer member 141 upwardly is sufficient to remove the biasing force of the helical springs 140 from the modified canister seat 50 allowing the modified canister seat 50 and the pressurized dispensing container 100 to move back upwardly within the actuator 1 under the internal spring bias of the pressurized dispensing container 100. Upward movement of the modified canister seat 50 brings the guide arms 155 into contact with the toggles 150 as shown in FIG. 27 which act to rotate the toggles into their original position as shown in FIG. 28. The upward movement of the modified canister seat 150 also re-engages the hook 53 with the slip hook 63 in the manner described above. Hence, at this point the dust cap 5 of the actuator 1 is still in the open position but the pressurized dispensing container 100 has been able to move back into its unloaded, non-actuated state as shown in FIG. 28. Thus, leakage of medicament and/or propellant from the container 100 via the outlet seals of the internal metering valve is prevented.

Figure 29:
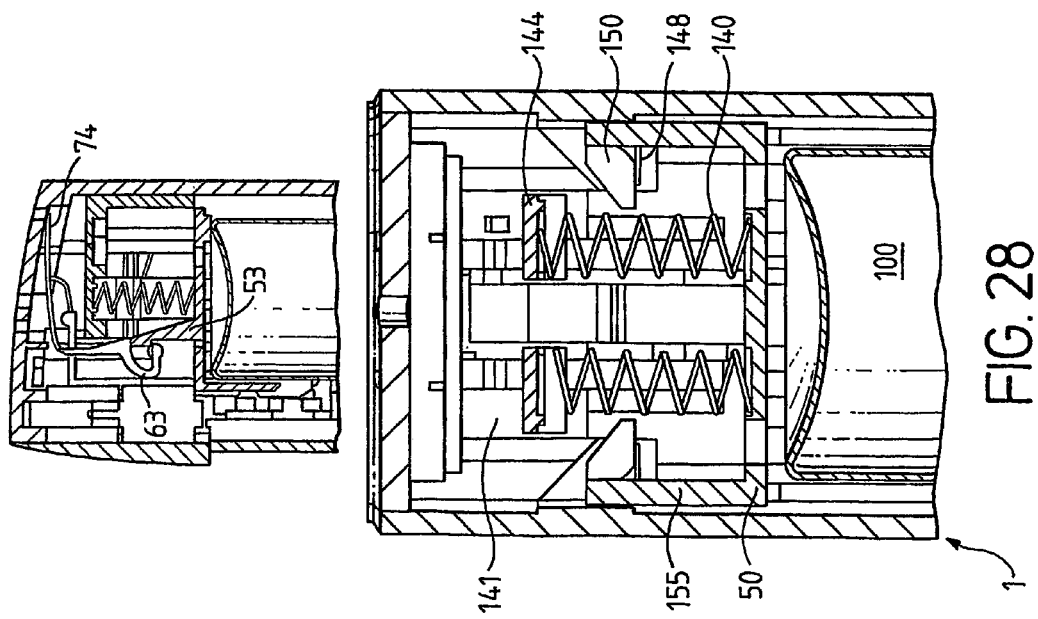
Figure 30:
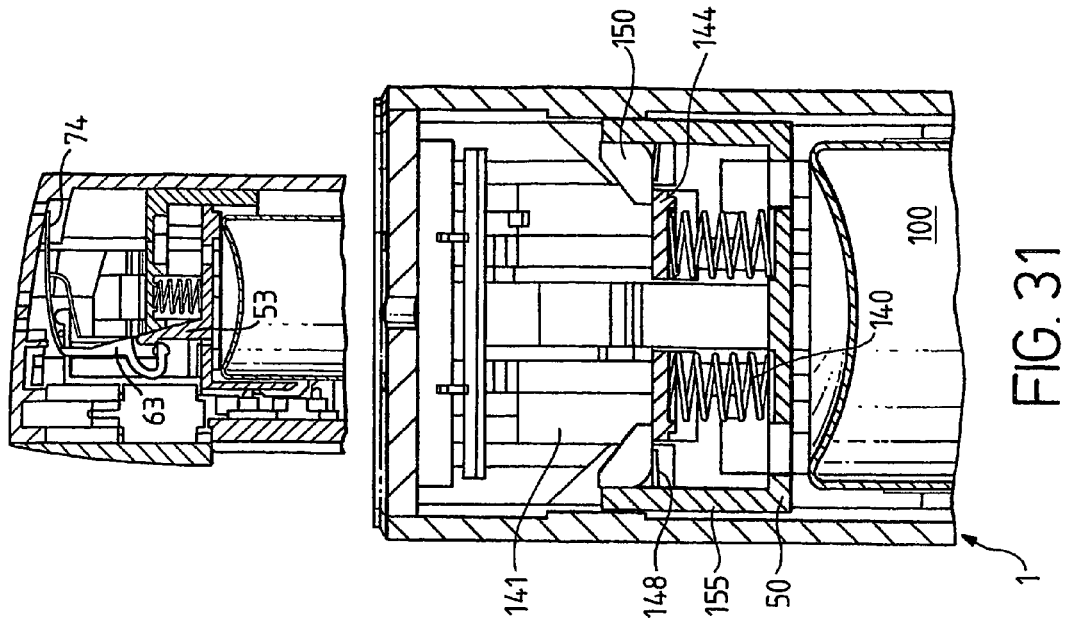
Figure 31:
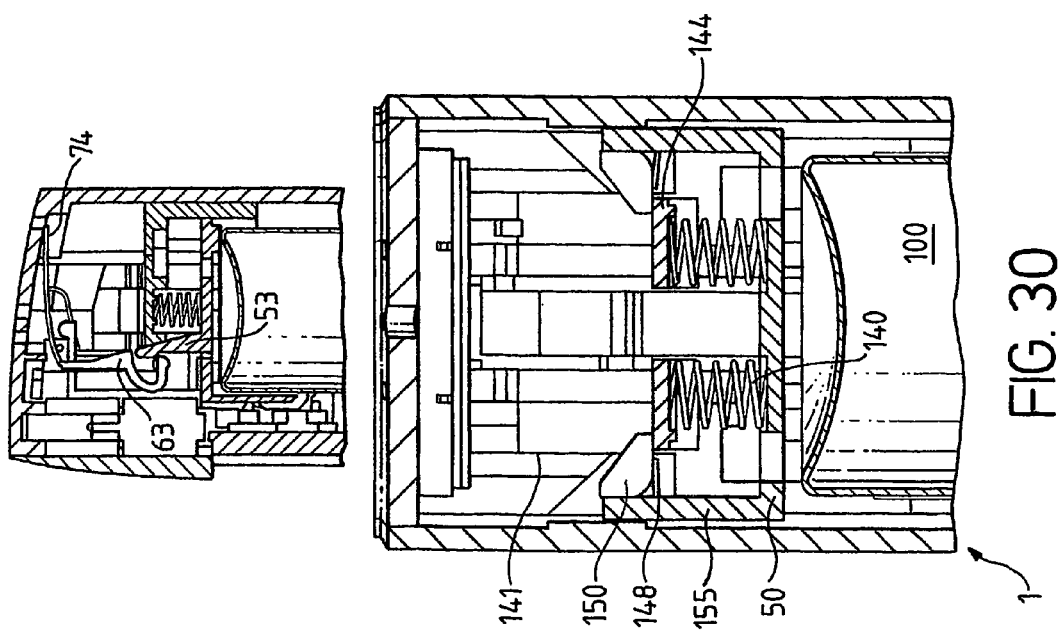

The mechanism is reset by closing the dust cap 5. As will be described below, rotation of the dust cap 5 moves the retainer member 141 downwardly within the actuator 1 towards the mouthpiece 4 resulting in the transverse platform 144 being pulled down between the toggles 150 as shown in FIG. 29. The toggles 150 are thus rotated into contact with and deflect small leaf springs 148 located immediately beneath each toggle 150. Once the transverse platform 144 of the retainer member 141 clears the toggles 150 the toggles are moved back into their original orientation by means of the leaf springs 148 as shown in FIG. 30. The final portion of the rotation of the dust cap 5 allows the retainer member 141 to move upwardly under the bias of the springs 140 to a small degree so that the toggles 150 re-engage the toggle catch surfaces 143 of the transverse platform 144. In this position, as shown in FIG. 31 the actuator 1 is ready for a further dispensation cycle.

Figure 32:
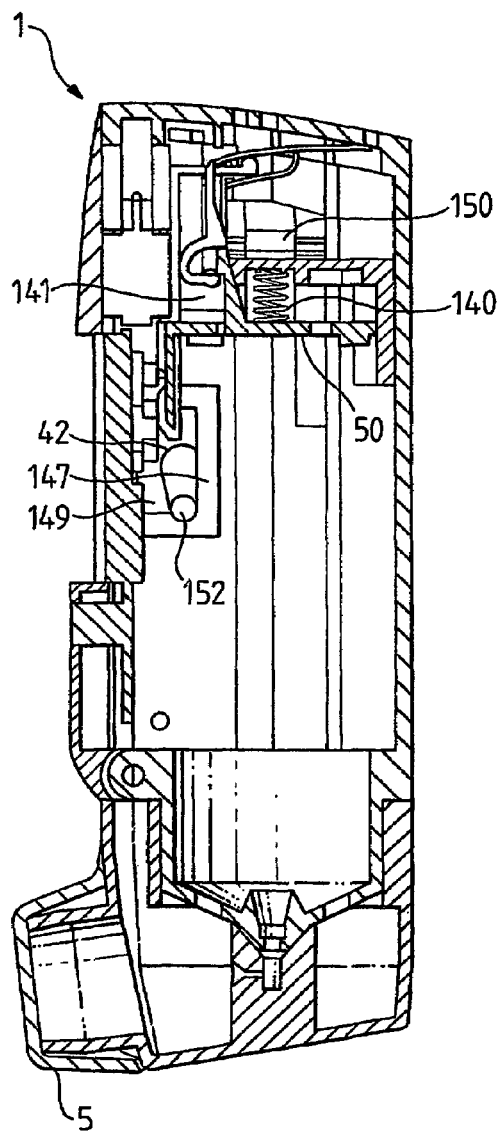
FIGS. 32 to 35 are cross-sectional views of the dispensing device of FIGS. 22 to 31 showing the re-setting of the device.

The mechanism for moving the retainer member 141 downwardly from the position of FIG. 28 into the position of FIG. 31 will now be explained. FIGS. 32 to 35 more clearly illustrate how closure of the dust cap 5 re-sets the retainer member 141 and the toggles 150 (the pressurised dispensing container has been omitted for clarity). As shown in FIG. 32, the retainer member 141 further comprises a lower arm 147 which extends downwardly within the interior of the actuator 1. Each arm 147 comprises an aperture 149 which engages a cam 152 provided on the bosses 42 of the dust cap 5 and which protrude into the interior of the actuator 1 through the apertures 10 formed in the front case 2.

Figure 33:
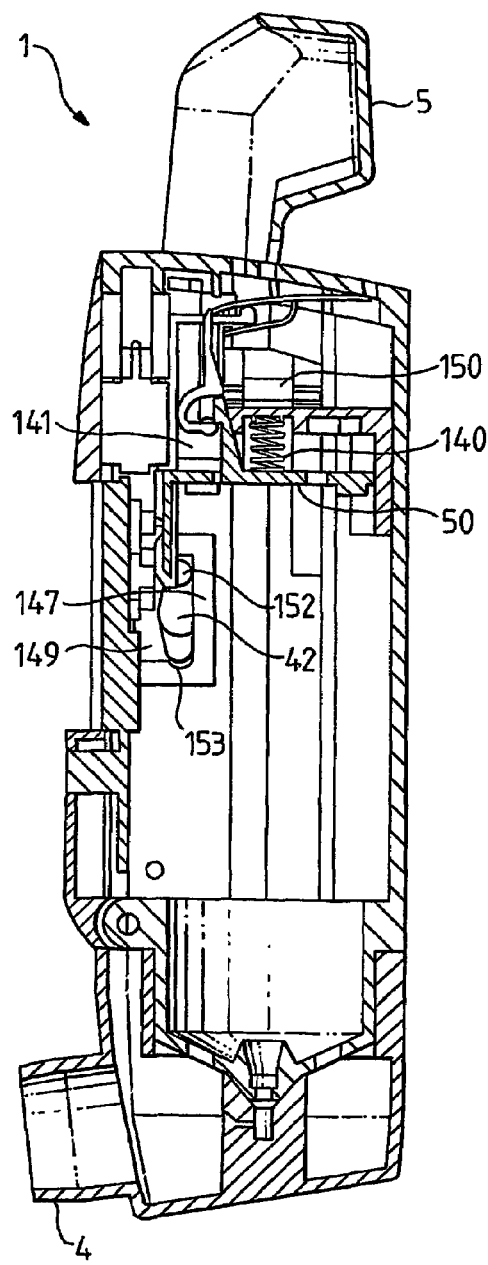
Figure 34:
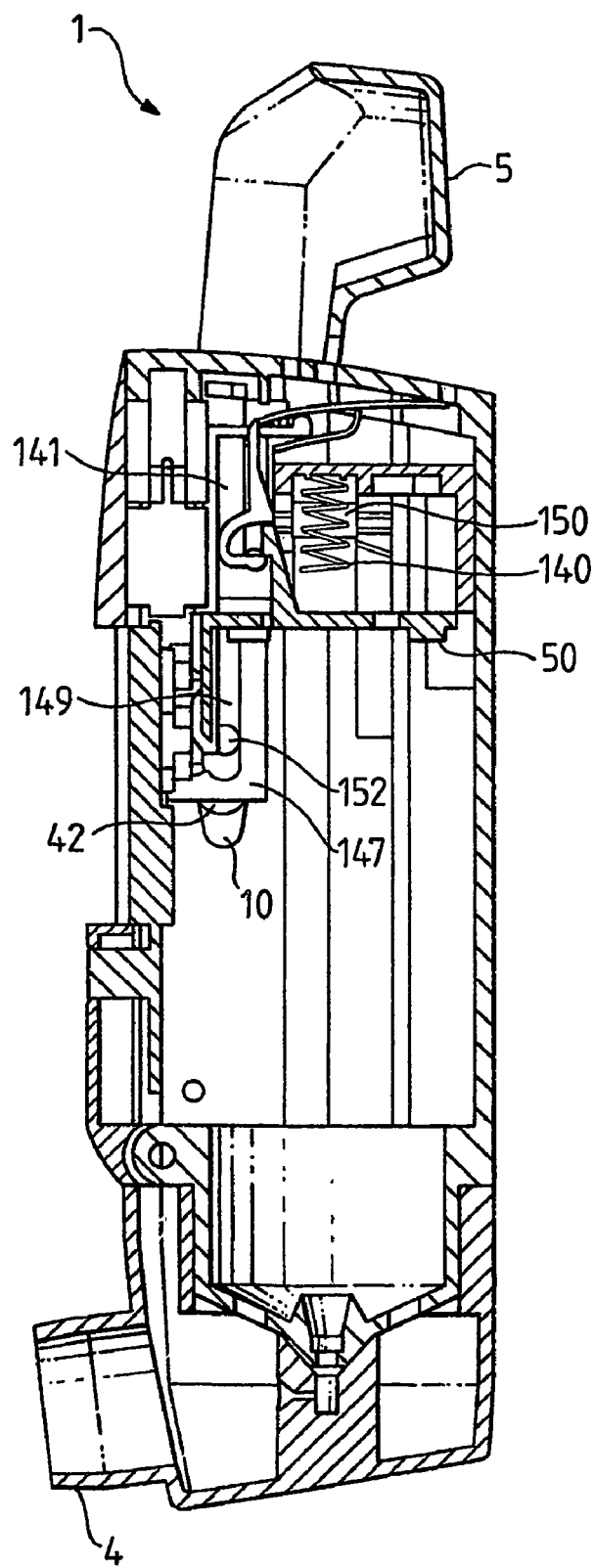

The aperture 149 of each lower arm 147 is generally rectangular but is provided with a recess 153 in which the cam 152 can nestle when the dust cap is in a closed position as shown in FIG. 32. FIG. 33 shows the dust cap 5 rotated into the open position and shows that the cam 152 has been moved upwardly relative to the lower arm 147 so that it is disengaged from the recess 153 and is located part way along the aperture 149. In this position as described above the retainer member 141 is held in position solely by the action of the toggles 150. FIG. 34 shows the actuator 1 immediately after dispensation of a dose but with the dust cap 5 still in the open position and equates to the position of FIG. 28. At this point the cam 152 is still out of engagement with the lower arm 147. However, as shown in FIG. 35, on rotation of the dust cap 5 into the closed position the cam 152 is brought into engagement with the lower arm 147 and moves the lower arm 147 and hence the remainder of the retainer member 141 downwardly. The presence of the recess 153 in the lower arm 147 allows the retainer member 141 to move back upwardly within the actuator 1 to a small degree just as the dust cap 5 is brought into the closed position discussed above in order to enable the toggles 150 to re-engage the toggle catch surfaces 143 of the transverse platform. In addition, the recess 153 provides a positive closure to the dust cap 5 that provides a small resistance to opening of the dust cap 5. This is useful in keeping the duct cap 5 securely in place.

It should be noted that the mechanism described herein for removing the valve load from the pressurised dispensing container 100 when the dust cap 5 is in the open position may be applied to either the first or second embodiments of actuator 1 described above and also to other actuators which may or may not incorporate a trigger mechanism 7 operated by the inhalation of a user.

FIGS. 37 to 41 illustrate schematically an alternative mechanism for removing the load from the valve of the pressurised dispensing container 100. The mechanism comprises a canister seat formed from a first part 50 which is retained by and released from the slip hook 63 in the way described above and a second part 510 fixed to the pressurised dispensing container 100. The first and second parts 50, 510 of the canister seat are slidable relative to one another and together define a pressurisable chamber 511. A vent 512 is provided from the chamber 511 which is closable by a flap valve 513. FIG. 37 shows the at rest position prior to inhalation. On inhalation the vane is rotated and the first part 50 of the canister seat is released and is moved downwards by action of the leaf spring 60. Air is unable to escape rapidly from the vent 512 due to the flap valve 513. Consequently the force is transferred to the second part 510 of the canister seat and the pressurised dispensing container 100 is moved downwards to cause it to operate. At the end of the downward stroke of the first part 50 the flap valve 513 contacts, and is lifted by, a reset sleeve 500 as shown in FIG. 39. At this point the pressurised air within the chamber 511 rapidly escapes via the vent 512 allowing the fixed part 510 and pressurised dispensing container 100 to move upwards under the bias of the container's internal metering valve. At this point the load is removed from the container 100. The mechanism is reset by rotating to close the dust cap which acts on the reset sleeve 500 via a cam to lift the reset sleeve 500 and first part 50 back into the position shown in FIG. 37. Alternatively, the vent 512 may be sized to limit the through flow of air and the flap valve 513 dispensed with. In operation, on triggering of the trigger mechanism the force is transferred to the second part 510 since the air cannot escape rapidly enough from the chamber 511. However after actuation the air vents through the still open 512 allowing the load to be removed as described above.

Figure 41:
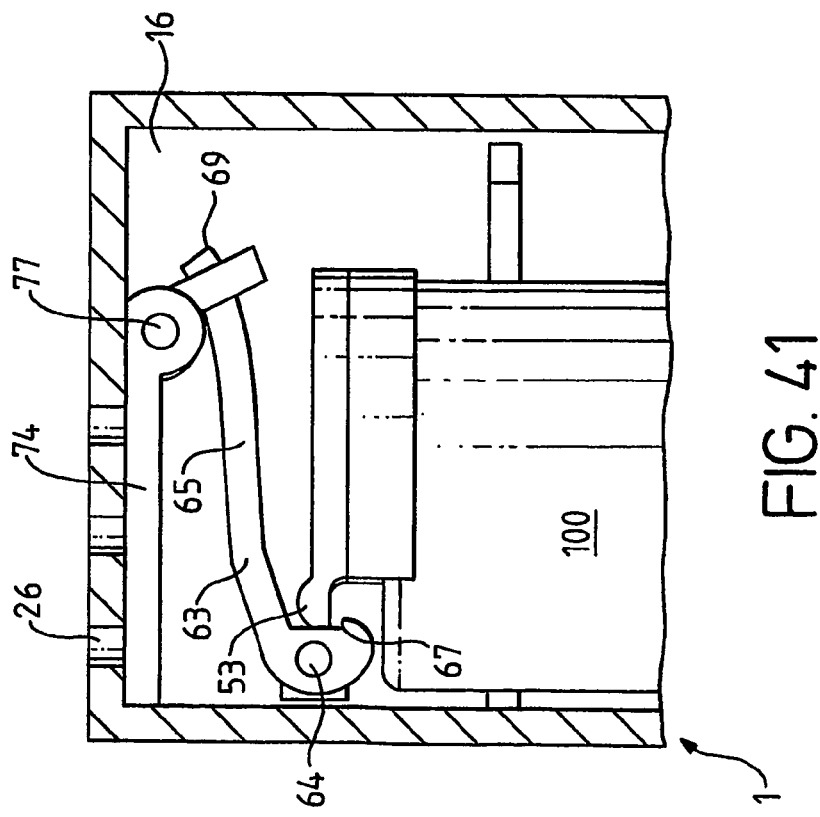
FIG. 41 is cross-sectional schematic view of an alternative trigger mechanism for use with the dispensing device of the present invention.

FIG. 41 schematically illustrates an alternative trigger mechanism which may be used with the actuator 1 of the present invention. In this alternative, the vane 74 is provided as before connected to the chassis 16 at a pivot point 77. The slip hook 63 is orientated substantially horizontally and is pivoted to the chassis 16 at a pivot point 64. As before, the slip hook 63 comprises an elongate arm 65 and a catch surface 67 for restraining a hook 53 of a canister seat 50. However, in this version, the elongate arm 65 of the slip hook 63 extends substantially horizontally and the distal end 69 is restrained in tension by a link extending below the vane 74. In operation, on inhalation by a user, the vane 74 rotates moving the link of the vane out of engagement with the distal end 69 of the slip hook 63 at which point the slip hook 63 is free to rotate in a clockwise direction as viewed in FIG. 41 freeing the hook 53 from the catch surface 67.

Figure 42:
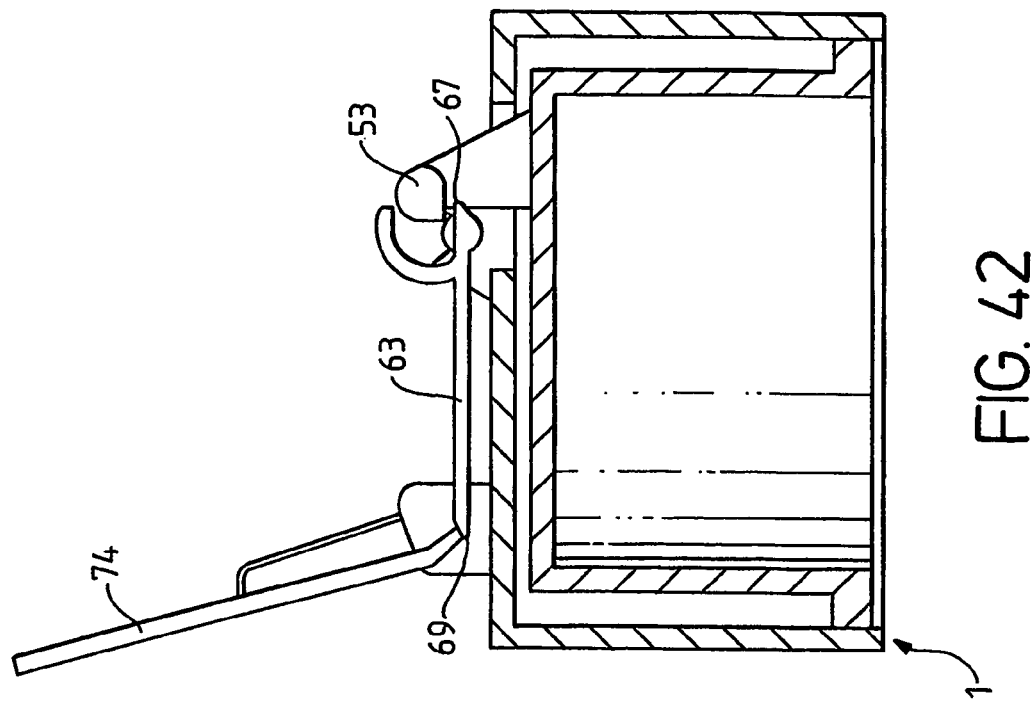
FIG. 42 is a perspective schematic view of a further alternative trigger mechanism for use with the dispensing device of the present invention.

FIG. 42 illustrates a further alternative trigger mechanism which may be used in the actuator 1 of the present invention. The configuration as shown in FIG. 42 is mechanically identical to that described above with reference to the first embodiment, except that the orientation of the vane 74 is now substantially vertical rather than substantially horizontal. In addition, the slip hook 63 is orientated in the armed position substantially horizontally. In other respects, operation of the trigger mechanism is the same as that described above in the first embodiment.

Figure 43:
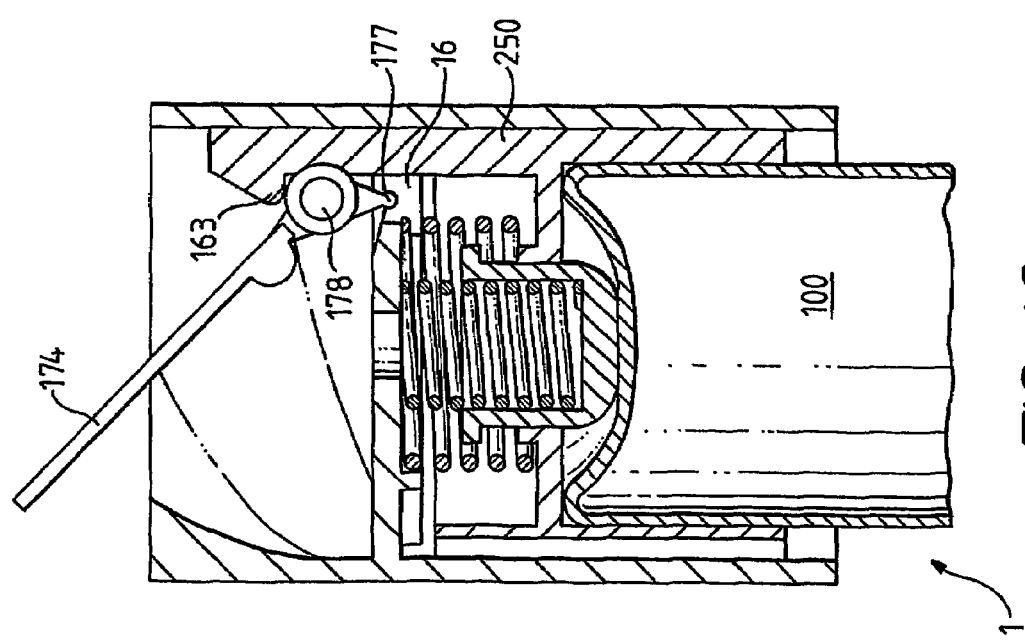
FIG. 43 is a cross-sectional schematic view of a further alternative trigger mechanism for use with the present invention.

FIG. 43 illustrates a further alternative trigger mechanism. In this mechanism, a vane 174 is provided pivoted about a pivot point 177 connected to the chassis 16 of the actuator 1. The vane 174 has a dog-legged configuration and is provided with a rotatable peg 178 at the angle of the dog-leg. A hook 163 is provided on a modified canister seat 250 which is engagable with the peg 178. In the position shown, the peg 178 prevents downward movement of the canister seat 250 and hence actuation of the actuator 1. On inhalation by a user, the vane 174 is rotated in an anti-clockwise direction as viewed in FIG. 43 causing the peg 178 to move out of engagement with the hook 163 allowing the modified canister seat 250 to move downwardly in the direction of the spring 260.

Figure 44:
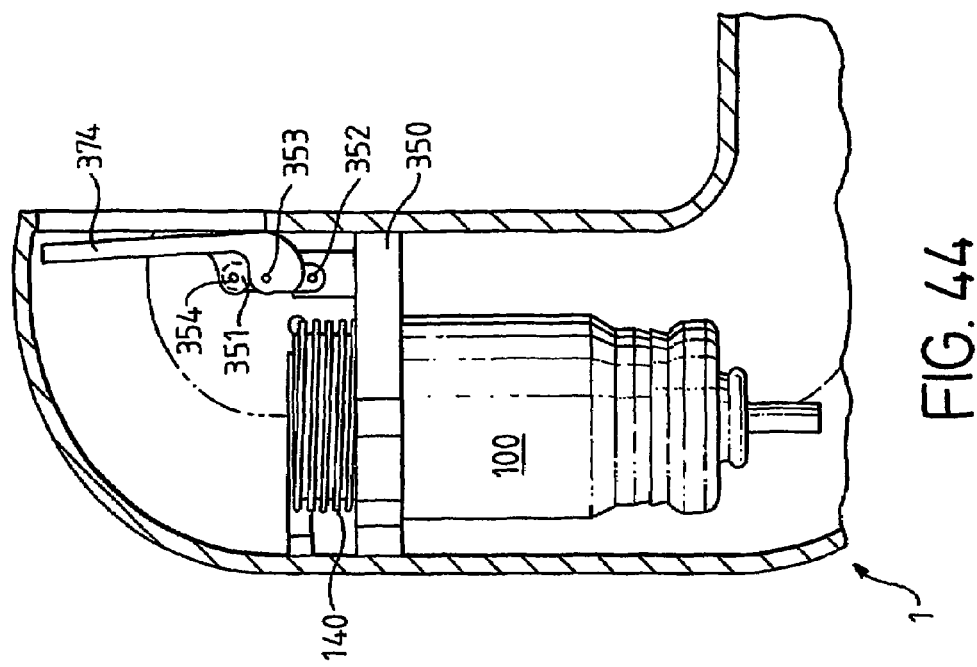
FIG. 44 is a cross-sectional schematic view of a further alternative trigger mechanism for use with the present invention.

FIG. 44 illustrates a further alternative trigger mechanism in which the pressurised dispensing container 100 is biased by means of a helical spring 140 acting on a canister seat 350. The canister seat 350 is pivotably connected to a link member 351 at a lower pivot point 352. A pivotable vane 374 is provided and pivots about a pivot point 353 mounted to the chassis 16 of the actuator 1. The vane 374 is also pivotably connected to the link member 351 at a top pivot point 354. In the rest position, the top pivot 354 lies over-centre with respect to the pivot point 353 and lower pivot 352, in other words to the right of a vertical line passing through the pivot point 353 as viewed in FIG. 44. On inhalation the vane 374 is rotated counter-clockwise moving the top pivot 354 past the vertical at which point the spring 140 accelerates the rotation of the vane and the canister seat 350 and pressurised dispensing container 100 are enabled to move downwards to actuate the container.

Figure 45:
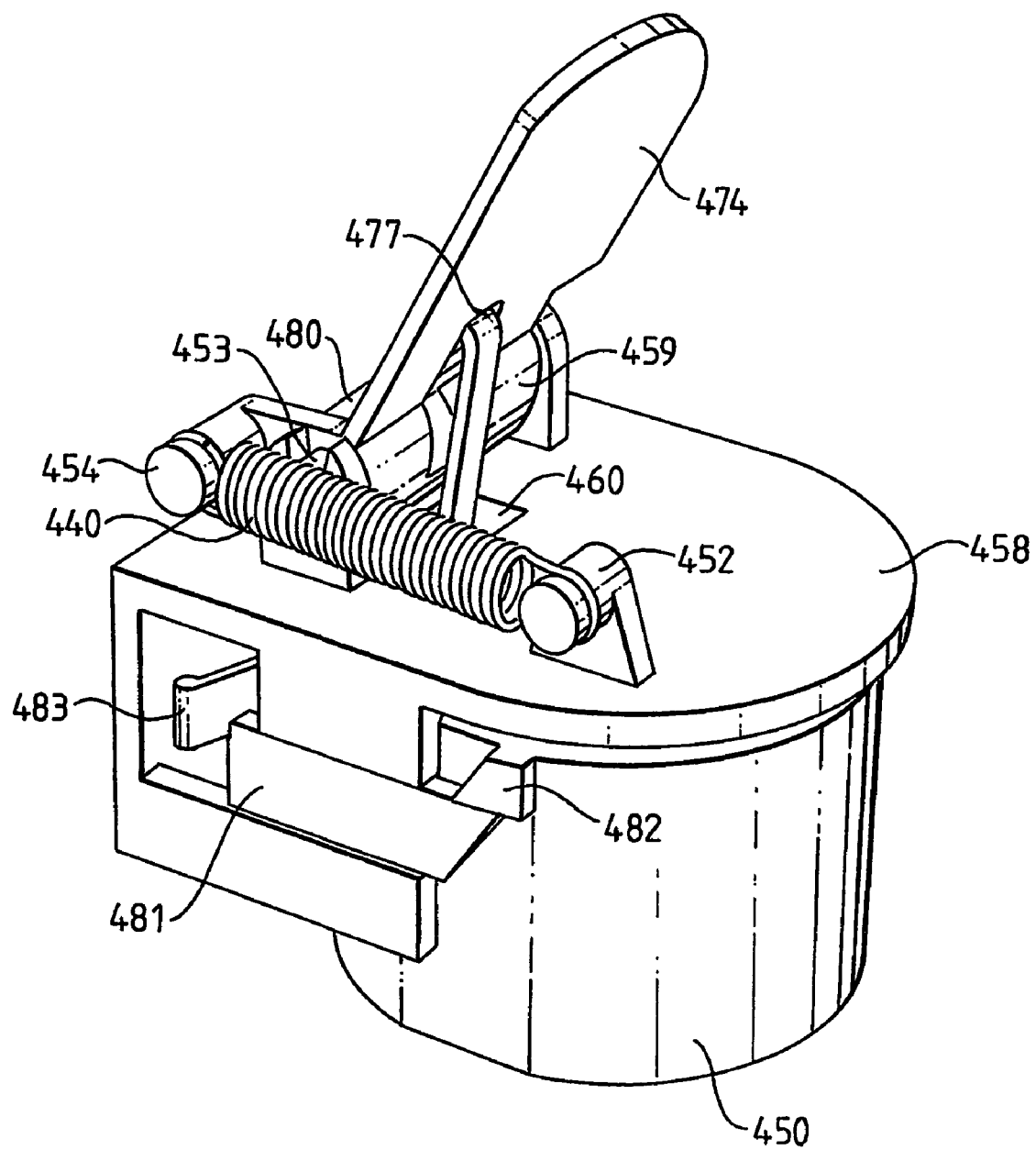
FIG. 45 is a cross-sectional schematic view of a further alternative trigger mechanism for use with the present invention.

FIG. 45 illustrates a further trigger mechanism comprising a chassis 458 pivotably connected to a vane 474 by means of a spring 440 spanning between a boss 452 on the chassis 458 and a boss 454 on the vane 474. The vane 474 is pivotable connected to the chassis about a pivot point 453. A canister seat 450 is provided comprising a hook 459 which passes up through an aperture 460 in the chassis 458 into the region of the vane 474. The chassis 458 houses a slidable sprung bar 481 which is biased by means of a sprung portion 483 in the rest position into engagement with a projection 482 on the canister seat 450 which prevents downward movement of the seat 450. On inhalation the vane 474 rotates clockwise as viewed in FIG. 45 moving the boss 454 over-centre at which point the spring 440 accelerates the rotation of the vane. A rear portion of the vane 474 is provided with a cam (not shown) which acts on the slidable sprung bar 481 to the left as viewed in FIG. 44 on rotation of the vane 474 to move the bar 481 out of engagement with the projection 482 and so enable downward movement of the canister seat 450 and operation of the dispensing container. On resetting the trigger mechanism the hook 459 of the canister seat 450 is moved upwards which rotates the vane 474 into its initial position. The vane 474 is provided with an aperture 477 which is shaped to ensure that the hook 459 detaches from the vane 474 as the trigger mechanism reaches the rest position.

In the above embodiments the resetting of the trigger mechanism 7 has been described as being achieved by rotation of the dust cap 5 causing in turn rotation of a cam surface or off-set peg engaged with a portion of the canister seat 50 or canister reset seat 130. However, resetting of the trigger mechanism 7 may equally be achieved by other means without departing from the scope of the present invention. For example, the canister seat 50 or canister reset seat 130 may be displaced by means of equivalent mechanical arrangements such as an axial slider, a rotatable lever, a rack and pinion operated by a key, or similar.

The above invention has been particularly described, by way of example, applied to a dispensing device actuated by the inhalation of a user. However, aspects of the invention such as the means for locking the housing, the user interface, and the means for locking-out operation of the trigger mechanism may be utilised with dispensing devices where triggering is other than by inhalation. In addition, the invention has been described with reference to a pressurised dispensing container but can be applied to other dispensing devices.

The invention claimed is:

1. Dispensing apparatus comprising a housing (2,3,4) for receiving in use a dispensing container (100) containing a product, the housing comprising an outlet (4) through which said product, in use, is dispensed, wherein the dispensing apparatus further comprises a spring for from actuating a dispensing container received in the housing and a trigger mechanism (7) for controlling the spring, the trigger mechanism comprising a pivotable member (74) rotatable from a first position to a second position, wherein the dispensing apparatus further comprises a lockout member (80) movable into and out of engagement with the pivotable member from a locked position, in which it engages a portion of the pivotable member to prevent rotation of the pivotable member from its first position to its second position, to an unlocked position, in which the pivotable member is free to rotate and wherein the lock-out member is movable by an electrically powered motor which moves the movable lock-out member into and out of engagement with the pivotable member.

2. Dispensing apparatus as claimed in claim 1 wherein the lock-out member comprises an elongate stem (61) movable axially within the housing (2,3) and a transverse arm (83) extending laterally from the elongate stem, wherein a distal end of the transverse arm is engagable with the pivotable member (74).

3. Dispensing apparatus as claimed in claim 1 wherein the pivotable member is a vane (74).

4. Dispensing apparatus as claimed in claim 3
wherein further comprising at least one air inlet (26) for entry of air into an interior of the housing, wherein the vane (74) is rotatable when suction is applied to the at least one air inlet to establish an air flow through the interior of the apparatus.

5. Dispensing apparatus as claimed in claim 1 wherein the lock-out member comprises a threaded portion which engages a threaded rotatable member (71) of the motor.

6. Dispensing apparatus as claimed in claim 1 further comprising control means (6) for controlling operation of the motor.

7. Dispensing apparatus as claimed in claim 6 wherein the control means comprises a control processor (95) mounted within the housing.

8. Dispensing apparatus as claimed in claim 7 wherein the control means further comprises one or more switches(93)

operable by the lock-out member to send signals to the control processor regarding the position of the lock-out member.

9. Dispensing apparatus as claimed in claim 8 wherein the lock-out member comprises one or more cam surfaces (84) for engaging and switching the one or more switches of the control means on movement of the lock-out member.

10. Dispensing apparatus as claimed in claim 1 wherein the lock-out member further comprises means (85) for locking a first part and a second part of the housing together.

11. Dispensing apparatus as claimed in claim 10 wherein the
lock-out member is mounted to one of the first or second parts of the housing and the means for locking the first and second parts together comprises a distal end (65) of the lock-out member which is engagable in a recess (23) in the other of the first or second parts.

12. Dispensing device as claimed in claim 1 further comprising a dispensing container (100).

13. Dispensing device as claimed in claim 1 wherein the dispensing container is a metered dose inhaler.

14. Dispensing device as claimed in claim 12 wherein the dispensing container contains a medicament for oral or nasal administration.

15. Dispensing device as claimed in any of claims 13 wherein the dispensing container includes a hydrofluoroalkane propellant.

16. A method of controlling operation of a dispensing apparatus according to claim 1, pivotable member rotatable from a first position to a second the method comprising the steps of:
moving a lock-out means from a locked position, in which rotation of the pivotable member from its first position to its second position is prevented, to an unlocked position, in which the pivotable member is free to rotate;
applying suction to an outlet of the dispensing apparatus to establish a flow of air from the at least one air inlet to the outlet to move the pivotable member from its first position to its second position to trigger the trigger mechanism to dispense a product from said dispensing container;
moving the lock-out means from the unlocked position back to the locked position to prevent further rotation of the pivotable member after resetting the dispensing apparatus.

17. A method of controlling the timing of actuation of a dispensing apparatus according to claim 1, comprising the steps of:- providing a timing mechanism;
starting the timing mechanism on a first actuation of the dispensing apparatus to commence timing of a first actuation 'window' of predetermined length;
optionally actuating the dispensing apparatus one or more times during the actuation 'window', wherein on each actuation of the dispensing container the timing of a further actuation 'window', is commenced;
wherein if a total number of actuations during any actuation 'window' reaches a predetermined number further actuation of the dispensing apparatus is prevented until the end of said actuation 'window'.

18. A method as claimed in claim 17 wherein successive actuations of the dispensing apparatus are prevented within a fixed time period of each other.

19. Dispensing apparatus comprising a housing for receiving in use a dispensing container containing a product, the housing comprising an outlet through which said product, in use, is dispensed, wherein the dispensing apparatus further comprises a spring for actuating a dispensing container received in the housing and a trigger mechanism for controlling the spring, the trigger mechanism comprising a pivotable member rotatable from a first position to a second position, wherein the dispensing apparatus further comprises a lock-out member movable into and out of engagement with the pivotable member from a locked position, in which it engages a portion of the pivotable member to prevent rotation of the pivotable member from its first position to its second position, to an unlocked position, in which the pivotable member is free to rotate, and wherein the lock-out member is movable by a device that is position controllable for movement of the lock-out member between extreme and intermediate fixed position relative to the travel of said lock-out member.

* * * * *